United States Patent
Hellwig et al.

(10) Patent No.: US 7,553,281 B2
(45) Date of Patent: Jun. 30, 2009

(54) INSULIN BOLUS RECOMMENDATION SYSTEM

(75) Inventors: Robert Hellwig, Borken (DE); Stefan Weinert, Pendleton, IN (US)

(73) Assignees: Roche Diagnostices Operations, Inc., Indianapolis, IN (US); Disetronic Licensing AG, Burgdorf (CH)

( * ) Notice: Subject to any disclaimer, the term of this patent is extended or adjusted under 35 U.S.C. 154(b) by 97 days.

(21) Appl. No.: 11/868,003

(22) Filed: Oct. 5, 2007

(65) Prior Publication Data
US 2008/0058628 A1   Mar. 6, 2008

Related U.S. Application Data

(62) Division of application No. 10/927,614, filed on Aug. 26, 2004, now Pat. No. 7,291,107.

(51) Int. Cl.
A61B 5/00 (2006.01)
A61M 31/00 (2006.01)

(52) U.S. Cl. .................. 600/365; 600/300; 604/48; 604/65; 604/66

(58) Field of Classification Search .............. 600/365; 604/31, 66
See application file for complete search history.

(56) References Cited

U.S. PATENT DOCUMENTS

| | | | |
|---|---|---|---|
| 5,713,856 A | 2/1998 | Eggers et al. | |
| 5,822,715 A | 10/1998 | Worthington et al. | |
| 6,352,505 B1 | 3/2002 | Bortz | |
| 6,379,301 B1 | 4/2002 | Worthington et al. | |
| 6,427,088 B1 | 7/2002 | Bowman, IV et al. | |
| 6,461,331 B1 | 10/2002 | Van Antwerp | |
| 6,471,675 B1 | 10/2002 | Rogers et al. | |
| 6,554,798 B1 | 4/2003 | Mann et al. | |
| 6,558,351 B1 * | 5/2003 | Steil et al. | 604/131 |
| 6,562,001 B2 | 5/2003 | Lebel et al. | |
| 6,571,128 B2 | 5/2003 | Lebel et al. | |
| 6,577,899 B2 | 6/2003 | Lebel et al. | |
| 6,579,280 B1 | 6/2003 | Kovach et al. | |

(Continued)

FOREIGN PATENT DOCUMENTS

EP   1759726 A2   3/2007

OTHER PUBLICATIONS

Mudallar, Sunder R., M.D. et al., Insulin Aspart (B28 APS-Insulin): A Fast-Acting Analog of Human Insulin, Diabetes Care, vol. 22, No. 9, Sep. 1999.

*Primary Examiner*—Patricia C Mallari
(74) *Attorney, Agent, or Firm*—Harnes & Thornburg LLP

(57) ABSTRACT

A system for recommending insulin bolus quantities to an insulin user includes a display unit and memory unit coupled to a control circuit with a user blood glucose target stored in the memory unit. The control circuit is programmed to receive the user's current blood glucose value, to determine and display via the display unit a recommended correction insulin bolus quantity if the current blood glucose value exceeds the blood glucose target, to compute a difference value as the current blood glucose value less the blood glucose target, and to produce a modified blood glucose target as a sum of the blood glucose target and the difference value for a lock-out time period if the difference value is positive. Additional correction insulin bolus quantities may be recommended during the lock-out time period if the user's current blood glucose value exceeds the modified blood glucose target.

14 Claims, 16 Drawing Sheets

U.S. PATENT DOCUMENTS

| | | |
|---|---|---|
| 6,585,644 B2 | 7/2003 | Lebel et al. |
| 6,635,049 B1 | 10/2003 | Robinson et al. |
| 6,641,533 B2 | 11/2003 | Causey, III et al. |
| 6,648,821 B2 | 11/2003 | Lebel et al. |
| 6,659,948 B2 | 12/2003 | Lebel et al. |
| 6,687,546 B2 | 2/2004 | Lebel et al. |
| 6,690,280 B2 | 2/2004 | Citrenbaum et al. |
| 6,691,043 B2 | 2/2004 | Ribeiro, Jr. |
| 6,733,471 B1 | 5/2004 | Ericson et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 2002/0002326 A1 | 1/2002 | Causey, III et al. |
| 2002/0087120 A1 | 7/2002 | Rogers et al. |
| 2002/0107476 A1* | 8/2002 | Mann et al. .................. 604/67 |
| 2002/0193679 A1 | 12/2002 | Malave et al. |
| 2003/0032867 A1 | 2/2003 | Crothall et al. |
| 2003/0048185 A1 | 3/2003 | Citrenbaum et al. |
| 2003/0055570 A1 | 3/2003 | Ribeiro, Jr. |
| 2003/0060765 A1 | 3/2003 | Campbell et al. |
| 2003/0069614 A1 | 4/2003 | Bowman, IV et al. |
| 2003/0114836 A1 | 6/2003 | Estes et al. |
| 2003/0130616 A1 | 7/2003 | Steil et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0199854 A1 | 10/2003 | Kovach et al. |
| 2003/0204274 A1 | 10/2003 | Ullestad et al. |
| 2003/0212364 A1 | 11/2003 | Mann et al. |
| 2004/0068230 A1 | 4/2004 | Estes et al. |
| 2004/0073095 A1 | 4/2004 | Causey, III et al. |
| 2004/0167464 A1 | 8/2004 | Ireland et al. |
| 2004/0220517 A1 | 11/2004 | Starkweather et al. |
| 2007/0060869 A1 | 3/2007 | Tolle et al. |
| 2007/0060870 A1 | 3/2007 | Tolle et al. |

* cited by examiner

FIG. 2E

| Time Blocks | 15:43 |
|---|---|

Time Block Overview

Block 1 (hrs) 0 0 : 0 0 - 0 7 : 0 0
Block 2 (hrs) 0 7 : 0 1 - 1 8 : 5 9
Block 3 (hrs) 1 9 : 0 0 - 2 3 : 5 9
Block 4 (hrs) 0 0 : 0 0 - 2 3 : 5 9
Block 5 (hrs) 0 0 : 0 0 - 2 3 : 5 9
Block 6 (hrs) 0 0 : 0 0 - 2 3 : 5 9

[Cancel] [Reset] [Accept]

FIG. 2F

| Setup BRS | 15:43 |
|---|---|

[ Initialization ]
[ Calculation Factors ]
[ Time Blocks ]
[ General Parameters ]
[ Optional Parameters ]

[Menu] [Back]

FIG. 2G

| General Parameters | 15:43 |
|---|---|

High bG Warning

If you entered a bG exceeding a certain level, your BRS provides a warning message to carefully control your metabolic situation.

Please specify a threshold bG (< = 250 mg/dl / 14 mmol/l) for a high bG warning to be displayed.

High bG warning (mmol/l)  1 4 . 0

[Cancel] [Reset] [Accept]

FIG. 2H

| General Parameters | 15:43 |
|---|---|

Low bG Alert

If you entered a bG below a certain level, your BRS provides an alert message to eat fast carbs without dosage calculation.

Please specify a threshold bG (> = 60 mg/dl / 3.5 mmol/l) to provide this alert message.

Low bG warning (mmol/l)  0 3 . 5

[Cancel] [Reset] [Accept]

| General Parameters | 15:43 |
|---|---|
| Meal Excursion Settings 1 | |

After food intake, bG levels usually increase even if a correct meal bolus has been administered.

Which is the maximal bG increase you want the BRS to tolerate without recommending a correction bolus dosage after meal bolusing?

Max bG increase (mmol/l)   [0][3].[0]

[Cancel] [Reset] [Accept]

| General Parameters | 15:43 |
|---|---|
| Meal Excursion Settings 2 | |

After meal bolusing, your BRS will calculate a correction bolus only if a bG of xxx mmol/l is exceeded.

For which period of time after administration of a meal bolus do you want your BRS to apply this rule?

Duration   (min) [0][9][0]

[Cancel] [Reset] [Accept]

| General Parameters | 15:43 |
|---|---|
| Meal Excursion Settings 3 | |

For xxx min after meal bolusing, your BRS will calculate a correction bolus only if a bG increase of xxx mmol/l is exceeded.

Above which level of carb intake do you want your BRS to apply this rule?

Threshold Carb Intake (gr)   [1][0]

[Cancel] [Reset] [Accept]

| General Parameters | 15:43 |
|---|---|
| Correction Lockout Time | |

Repeated correction for one and the same event and level of bG excursion might result in a hypoglycaemia.

For which period of time do you want your BRS not to calculate a repeated correction bolus dosage?

Correc. Lockout Time (min) [0][9][0]

[Cancel] [Reset] [Accept]

Setup BRS | 15:43
- Initialization
- Calculation Factors
- Time Blocks
- General Parameters
- Optional Parameters

[Menu] [Back]

Optional Parameters | 15:43
Adjustment Levels

Your BRS offers you to define up to three pre-set adjustment levels, e.g. for sports, driving, disease, etc. Using the BRS, you can select for one of these levels and adapt the calculated recommendation accordingly.

Do you want to define pre-set adjustment levels?

[No] [Yes]

Optional Parameters | 15:43
Adjustment Level 1/3

Please assign a name to adjustment level 1:
Level 1                    [OK]

Please assign an adjustment in % to "Level 1":
    [%] +/- [0][0][0]⇕    [OK]

[Cancel] [Reset] [Accept]

Optional Parameters | 15:43
Adjustment Level 3/3

Please attribute a name to adjustment level 3:
Driving                    [OK]

Please attribute an adjustment in % to "Driving":
    [%] - [0][6][0]⇕    [OK]

[Cancel] [Reset] [Accept]

INSULIN BOLUS RECOMMENDATION SYSTEM

CROSS REFERENCE TO RELATED APPLICATION

This application is a divisional application of U.S. Patent application Ser. No. 10/927,614, filed on Aug. 26, 2004, now U.S. Pat. No. 7,291,107.

FIELD OF THE INVENTION

The present invention relates generally to techniques for managing blood glucose levels in diabetic individuals, and more specifically to systems for determining and recommending insulin administration as a way of managing blood glucose levels.

BACKGROUND

A number of handheld systems for managing diabetes care currently exist. It is desirable with such handheld systems to provide for the determination and recommendation of additive correction insulin bolusing to closely track and satisfy the user's insulin needs. It is further desirable to provide for such additive correction insulin bolusing before, during and after meal bolusing, while also allowing for natural but manageable blood glucose increases resulting from carbohydrate intake.

SUMMARY

The present invention may comprise one or more of the features recited in the appended claims or one or more of the following features and combinations thereof. A system for recommending insulin bolus quantities to an insulin user may comprise a data input device, a display unit and a memory unit. A user blood glucose target may be established by storing the user blood glucose target in the memory unit. A method for recommending insulin bolus quantities may comprise the steps of receiving a current blood glucose value of the user, determining a recommended insulin bolus quantity if the current blood glucose value exceeds the blood glucose target, computing a difference value as the current blood glucose value less the blood glucose target, and increasing the blood glucose target by the difference value for a lock-out time period if the difference value is positive.

Alternatively or additionally, a method for recommending insulin bolus quantities may comprise the steps of receiving a current blood glucose value of the user at a first time instant, determining a first recommended insulin bolus quantity if the current blood glucose value taken at the first time instant exceeds the initial blood glucose target, computing a first difference value as the current blood glucose value of the user at the first time instant and the initial blood glucose target, computing a first modified blood glucose target as a sum of the initial blood glucose target and the first difference value, receiving a current blood glucose value from the user at a second time instant after the first time instant and after the first recommended insulin bolus quantity is administered to the user but before expiration of a first lock-out time period since the first time instant, and determining a second recommended insulin bolus quantity for the user if the current blood glucose value at the second time instant exceeds the first modified blood glucose target.

The method may further include the steps of computing a second difference value as the current blood glucose value of the user at the second time instant less the first modified blood glucose target, and computing a second modified blood glucose target as a sum of the first modified blood glucose target and the second difference value. The method may further still include the steps of receiving a current blood glucose value from the user at a third time instant after the second time instant and after the second recommended insulin bolus quantity is administered to the user but before expiration of the first lock-out time period since the first time instant and before expiration of a second lock-out time period since the second time instant, and determining a third recommended insulin bolus quantity for the user if the current blood glucose value at the third time instant exceeds the second modified blood glucose target. The method may yet further include the steps of computing a third difference value as the current blood glucose value of the user at the third time instant less the second modified blood glucose target, and computing a third modified blood glucose target as a sum of the second modified blood glucose target and the third difference value.

Alternatively, the method may further include the steps of receiving a current blood glucose value from the user at a third time instant after the second time instant, after the second recommended insulin bolus quantity is administered to the user and after expiration of the first lock-out time period since the first time instant, but before expiration of a second lock-out time period since the second time instant, computing a third modified blood glucose target as the second modified blood glucose target less the first difference value, and determining a third recommended insulin bolus quantity for the user if the current blood glucose value at the third time instant exceeds the third modified blood glucose target. The method may further still include the steps of computing a third difference value as the current blood glucose value of the user at the third time instant less the third modified blood glucose target, and computing a fourth modified blood glucose target as a sum of the third modified blood glucose target and the third difference value.

Alternatively or additionally, a method for recommending insulin bolus quantities to an insulin user may comprise the steps of establishing a blood glucose target for the user, receiving a carbohydrate value indicative of a quantity of carbohydrates that will be subsequently ingested by the user, determining a recommended compensation insulin bolus quantity as a function of the carbohydrate value, and increasing the blood glucose target by a post-prandial increase value to produce a first modified blood glucose target for a post-prandial lock-out time period if the carbohydrate value exceeds a threshold value. The method may further include the steps of receiving a first current blood glucose value of the user after administering the recommended compensation insulin bolus to the user but before expiration of the post-prandial lock-out time period, determining a first recommended correction insulin bolus quantity if the first current blood glucose value exceeds the first modified blood glucose target, computing a first difference value as the first current blood glucose value less the first modified blood glucose target, and increasing the blood glucose target by the first difference value to produce a second modified blood glucose target for a first correction lock-out time period if the first difference value is positive. The method may further still include the steps of receiving a second current blood glucose value of the user after administering the recommended compensation insulin bolus to the user, after administering the first recommended correction insulin bolus to the user, and after expiration of the post-prandial lock-out time period, but before expiration of the first correction lock-out time period, reducing the second modified blood glucose target by the post-prandial increase value to produce a third modified blood glucose target, determining a second recommended correction insulin bolus quantity if the second current blood glucose value exceeds the third modified blood glucose target, computing a second difference value as second current blood glucose value less the third modified blood glucose target, and increasing the blood glucose target by the second difference value to produce a fourth modified blood glucose target for a second correction lock-out time period if the second difference value is positive.

Alternatively or additionally, a method for recommending insulin bolus quantities to an insulin user may comprise the steps of establishing a blood glucose target for the user, receiving a first current blood glucose value of the user and a carbohydrate value indicative of a quantity of carbohydrates that will be subsequently ingested by the user, determining a recommended compensation insulin bolus quantity as a function of the carbohydrate value, determining a first recommended correction insulin bolus quantity if the first current blood glucose value exceeds the blood glucose target, increasing the blood glucose target by a post-prandial increase value for a post-prandial lock-out time period if the carbohydrate value exceeds a threshold value, and increasing the blood glucose target by a first difference value, computed as the first current blood glucose value less the blood glucose target, for a first correction lock-out time period if the first difference value is positive. The blood glucose target, increased by the post-prandial increase value, the first difference value, or both, corresponds to a first modified blood glucose target.

The method may further include the steps of receiving a second current blood glucose value of the user after administering the recommended compensation insulin bolus quantity and the recommended first correction insulin bolus quantity to the user, but before expiration of the post-prandial lock-out time period and before expiration of the first correction lock-out time period, determining a second recommended correction insulin bolus quantity if the second current blood glucose value exceeds the first modified blood glucose target, computing a second difference value as the second current blood glucose value less the first modified blood glucose target, and increasing the blood glucose target by the second difference value to produce a second modified blood glucose target for a second correction lock-out time period if the second difference value is positive.

Alternatively, the method may further include the steps of receiving a second current blood glucose value of the user after administering the recommended compensation insulin bolus quantity and the recommended first correction insulin bolus quantity to the user, and after expiration of the post-prandial lock-out time period, but before expiration of the first correction lock-out time period, decreasing the first modified blood glucose target by the post-prandial increase value to produce a second modified blood glucose target, determining a second recommended correction insulin bolus quantity if the second current blood glucose value exceeds the second modified blood glucose target, computing a second difference value as the second current blood glucose value less the second modified blood glucose target, and increasing the second modified blood glucose target by the second difference value to produce a third modified blood glucose target for a second correction lock-out time period if the second difference value is positive.

These and other features of the present invention will become more apparent from the following description of the illustrative embodiments.

DESCRIPTION OF THE ILLUSTRATIVE EMBODIMENTS

Figure 1:
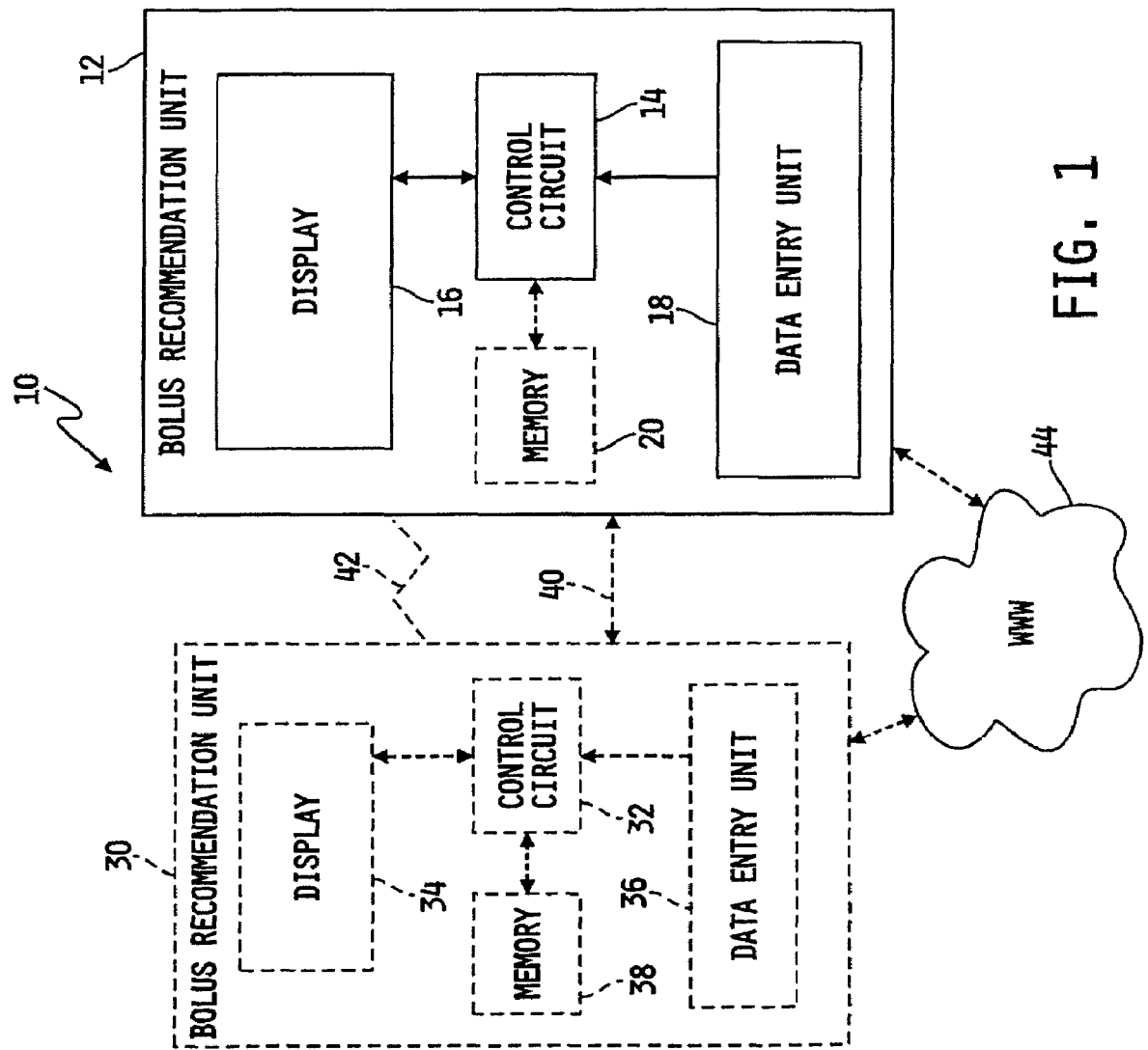
FIG. 1 is a block diagram of one illustrative embodiment of an insulin bolus recommendation system.

For the purposes of promoting an understanding of the principles of the invention, reference will now be made to a number of illustrative embodiments illustrated in the drawings and specific language will be used to describe the same.

Referring now to FIG. 1, a block diagram of one illustrative embodiment of an insulin bolus recommendation system 10 is shown. In the illustrated embodiment, the insulin bolus recommendation system 10 includes a bolus recommendation unit 12 having at least a control circuit 14 electrically connected to a visual display unit 16 and also to a data entry unit 18. The control circuit 14 may illustratively be a conventional, microprocessor-based control computer capable of executing one or more software algorithms, although the control circuit 14 may alternatively be any single one or collection of electronic circuits capable of operation as described hereinafter. In some embodiments, the control circuit 14 may be electrically connected to a conventional memory unit 20 as shown in phantom. The visual display unit may be or include any conventional display screen including, but not limited to, a cathode ray tube (CRT) display, a liquid crystal display (LCD), a plasma display, a single or multicolor monitor, a touch-sensitive data entry screen, or the like. The data entry unit 18 may be or include any conventional data input device including, but not limited to, a key board or key pad, a mouse or similar point-and-click device, one or more coded or non-coded, touch-sensitive switches associated with the display unit 16, a voice-activated data input device, or the like.

The insulin bolus recommendation system 10 may, in some embodiments, further include an additional bolus recommendation unit 30 as shown in phantom in FIG. 1. The unit 30 may include a control circuit 32 electrically connected to a visual display unit 34 and also to a data entry unit 36, wherein the control circuit 32, display unit 34 and data entry unit 36 may be provided in any of the forms described hereinabove with respect to the bolus recommendation unit 12. The control circuit 32 may further be electrically connected to a conventional memory unit 38. In this embodiment, the bolus recommendation unit 12 and the bolus recommendation unit 30 may be each configured to share information via a wired connection 40 including one or more signal paths physically connecting the two units, via a wireless signal path 42 such as a radio signal or cellular telephone link, and/or via the worldwide-web (WWW) 44, each using conventional technology.

The insulin bolus recommendation system 10 is configured to determine and recommend one or more injections of specific insulin bolus quantities into the blood stream of a user of the system 10 according to an insulin bolus recommendation protocol embodied in the system 10 as one or more executable software algorithms. The physical structure of the insulin bolus recommendation system 10 for executing such software algorithms and for communicating useful information between the system 10 and the user may take various forms. In one illustrative embodiment, for example, the bolus recommendation system 10 includes only the bolus recommendation unit 12 embodied as a conventional personal computer (PC), laptop or notebook computer, personal data assistant (PDA) or the like, or as a hand-held, lap top or desk top application-specific bolus recommendation unit. In any of these cases, the bolus recommendation unit 12 includes the memory unit 20 having the number of executable software algorithms stored therein, and the control circuit 14 is operable to execute these software algorithms to determine and recommend one or more injections of specific insulin bolus quantities into the blood stream of the user according to an insulin bolus recommendation protocol as will be described in detail hereinafter. In this embodiment, the display unit 16 is controlled by the control circuit 14 under the direction of the software algorithms to communicate information to the user and to prompt the user for information that the user may enter via the data entry unit 18.

In another illustrative embodiment, the insulin bolus recommendation system 10 includes the bolus recommendation unit 12 and the bolus recommendation unit 30. As one example of this embodiment, the bolus recommendation unit 12 may be a PDA or application-specific bolus recommendation unit as described hereinabove, and the bolus recommendation unit 30 may be a PC, laptop or notebook computer. In this embodiment, the unit 12 may communicate with the unit 30 either via the wireless interface 42 or via the wired interface 40 that may be electrically connected to a PDA or application-specific bolus recommendation unit cradle configured to receive the unit 12 and electrically connect the unit 12 in data communications with the unit 30. In this example, the memory units 20 and 38 of the units 12 and 30 respectively may each have the number of software algorithms stored therein, and the user may use the bolus recommendation unit 12 as a mobile insulin bolus recommendation unit and/or use the bolus recommendation unit 30 as a stationary insulin bolus recommendation unit. In this case, the user will maintain the databases of each unit 12 and 30 current by periodically synchronizing the databases of both units 12 and 30 via the wired or wireless interface 40 or 42 respectively.

As another example of the embodiment of the insulin bolus recommendation system 10 that includes the bolus recommendation unit 12 and the bolus recommendation unit 30, the bolus recommendation unit 12 may be a PDA, PC, laptop or notebook computer, cellular telephone or any other unit or device capable of accessing the WWW 44. In this example, the bolus recommendation unit 12 need not have the number of software algorithms stored in the memory unit 20, and need not include the memory unit 20 at all. The bolus recommendation unit 30 may, in the example, be a remote computer or conventional web server also configured to access the WWW 44 and having the number of software algorithms stored in the memory unit 38. The control circuit 32 of the remote computer or web server 30 is operable in this example to execute the number of software algorithms based on information provided over the WWW 44 by the user via the bolus recommendation unit 12. In this particular embodiment, the user and/or a health care provider may access a web page or web site controlled by the bolus recommendation unit 30 and provide the initial operating parameters and/or limits for the insulin bolus recommendation protocol to the control circuit 32. The user may then and thereafter access the web page or web site and enter current blood glucose information, and the control circuit 32 may then determine and recommend via the web page or web site one or more injections of specific insulin bolus quantities into the users blood stream, based on the current blood glucose information according to the insulin bolus recommendation protocol that will be described in detail hereinafter.

In this particular embodiment, the insulin bolus recommendation software algorithms thus reside in the remote computer or web server 30, and in this regard the bolus recommendation unit 12 need only include sufficient hardware so as to be capable of providing current blood glucose information to the web page or web site and of viewing the recommendation results produced on the web page or web site by the remote computer or web server 30. As a practical matter, though, it may further be desirable in this embodiment to provide the bolus recommendation unit 12 with the memory unit 20 and store the number of bolus recommendation software algorithms therein so that the bolus recommendation unit 12 may independently execute these software algorithms when it may not be possible or practicable to access the WWW 44 and/or the appropriate web page or web site. It will further be desirable in such an embodiment to provide for the synchronization of the remote and/or web-based database with the database stored in the memory unit 20 of the bolus recommendation unit 12.

It will be appreciated that the insulin bolus recommendation system 10 may be configured to cooperate with a glucose meter or other automatic blood glucose determination unit and/or an insulin pump or other automatic insulin dosing or administering unit. In embodiments wherein a glucose meter or other automatic blood glucose determination unit is included with the insulin bolus recommendation system 10, the control computer 14 may be configured to prompt such a unit, using conventional techniques, to automatically produce current blood glucose information which the system 10 may then use, as will be described in detail hereinafter, to determine and recommend administering one more insulin bolus quantities. In embodiments wherein an insulin pump or other automatic insulin dosing unit is included with the insulin bolus recommendation system 10, the control computer 14 may be configured to prompt such a unit, using conventional techniques, to automatically administer recommended insulin bolus quantities to the user.

As described hereinabove, the insulin bolus recommendation system 10 illustrated in FIG. 1 is operable to execute a number of software algorithms for determining and recommending administering of one or more of specific insulin bolus quantities into the blood stream of the user according to an insulin bolus recommendation protocol. At least one of these software algorithms is configured to establish, based on user and/or health care provider input, initial operating parameters and limits for use by an insulin bolus recommendation software algorithm. Referring now to FIGS. 2A-2N and 2P-2Q, a number of interactive display screens are shown that together form a graphical user interface illustrating one embodiment of such a software algorithm that is executable by the system 10 of FIG. 1 for establishing the initial operating parameters and limits for use by an insulin bolus recommendation software algorithm. It will be understood that the process illustrated in FIGS. 2A-2N and 2P-2Q is embodied in one or more software algorithms stored in one or both of the memory units 20 and 38, and is executable by the control circuit 14 and/or 32, and that the control circuit 14 and/or 32 is configured to control the display 16 and/or 34 respectively in a conventional manner to produce the graphical information illustrated in FIGS. 2A-2N and 2P-2Q. It will be further understood that the user prompts displayed on the display 16 and/or 32 may be responded to by a user of the system 10 by entering appropriate information in a conventional manner via the data entry unit 18 and/or 36 respectively.

In any case, the one or more software algorithms executed by the system 10 of FIG. 1 for establishing the initial operating parameters and limits for use by an insulin bolus recommendation software algorithm are illustrated in FIGS. 2A-2N and 2P-2Q as being implemented with the bolus recommendation unit 12 provided in the form of a conventional or application-specific PDA. Those skilled in the art will recognize that the illustrative process shown in FIGS. 2A-2N and 2P-2Q may alternatively be implemented with the bolus recommendation unit 12 and/or bolus recommendation unit 30 provided in any one or more of the physical forms described hereinabove.

Figure 2A:
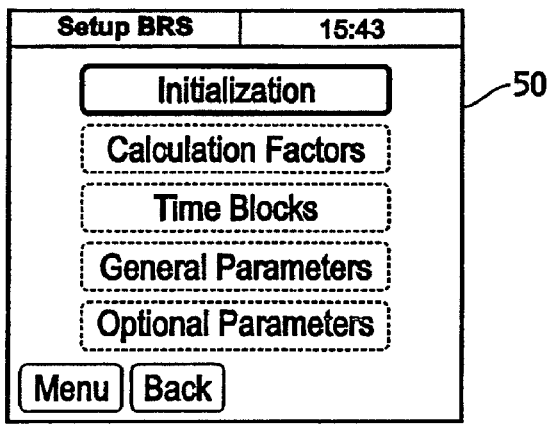
FIGS. 2A-2N and 2P-2Q, are each interactive display screens that together form a graphical user interface illustrating one embodiment of a software algorithm, executable by the system of FIG. 1, for establishing initial operating parameters and limits for an insulin bolus recommendation software algorithm.

Referring now to FIG. 2A, the one or more software algorithms for establishing the initial operating parameters and limits for use by an insulin bolus recommendation software algorithm begin with selection of a main set up screen 50. The main set up screen 50 displays the words "Setup BRS" in the upper left hand portion of the screen, indicating selection of the bolus recommendation system set up process. The system 10 includes a real-time clock, and the current time of day is indicated in the upper right hand portion of the screen 50. Some embodiments of the system 10 may include conventional circuitry for automatically adjusting or changing the time setting of the real-time clock, and other embodiments may allow the user to change the time setting of the real-time clock. It will be appreciated that various forms of the system 10 may be configured to deal differently with such user or automatic changes in the time setting of the real-time system clock. For example, in embodiments of the system 10 that are equipped to log or acknowledge time change events and time change amounts, one or more algorithms may be included to track such time change events and to update time-stamped data and/or other time-of-day sensitive information with the time change information. Similarly, in embodiments of the system 10 that are equipped to log or acknowledge time change events but not time change amounts, one or more algorithms may be included to track such time change events, to prompt the user for information relating to the time change amount, and to update time-stamped data and/or other time-of-day sensitive information with the time change information. Any such one or more algorithms would be within the abilities of a skilled software programmer.

The main portion of the screen 50 includes a number of functions, some of which may be immediately selectable and others which may not. In the example illustrated in FIG. 2A, the "Initialization" function is highlighted for selection, while the remaining features are shown outlined by dashed-line blocks indicating that these features are not yet selectable. Generally, the example initialization process illustrated in FIGS. 2A-2N and 2P-2Q requires sequential execution of the various features illustrated in FIG. 2A, and the features following the currently highlighted feature therefore may not be selectable until all preceding features have been selected and executed. It will be appreciated, however, that such a sequential feature execution process is illustrated in FIGS. 2A-2N and 2P-2Q only by way of example, and that the one or more software algorithms for establishing the initial operating parameters and limits for use by an insulin bolus recommendation software algorithm may alternatively be implemented in a non-sequential process.

Figure 2B:
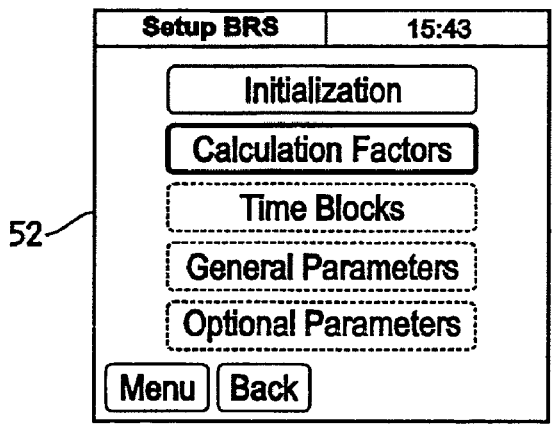
Figure 2C:
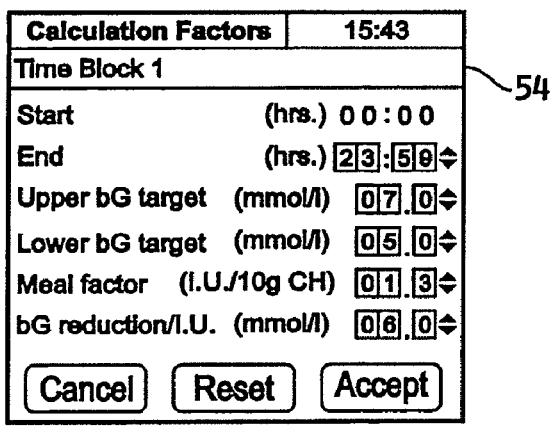

When the user selects the "Initialization" feature illustrated in FIG. 2A, the "Calculation Factors" feature then becomes highlighted as shown in the display 52 illustrated in FIG. 2B. When the "Calculation factors" feature is then selected, the "Calculation factors" display 54 is produced as shown in FIG. 2C. As long as the "Calculation factors" display 54 is selected, the display 54 displays the words "Calculation Factors" in the upper left hand portion of the screen, indicating selection of the calculation factors set up process.

The process illustrated in FIGS. 2A-2N and 2P-2Q provides for the establishment of initial operating parameters and limits for each of a number of time blocks, wherein the user may partition any day into any number (up to "N," e.g., N=6) time blocks. For each time block, the user may then input to the display 54 an upper blood glucose target (BGU), a lower blood glucose target or low blood glucose warning value (BGL), a meal factor (MF), and a blood glucose reduction-to-insulin ratio or insulin sensitivity value (IS). The upper blood glucose target (BGU) corresponds to a desired target blood glucose level, the low blood glucose warning value (BGL) corresponds to a blood glucose threshold below which the system will produce a low blood glucose warning as will be described in greater detail hereinafter with respect to FIG. 4C, the meal factor (MF) corresponds to a user-specific insulin-to-carbohydrate ratio, and the insulin sensitivity (IS) corresponds to a user-specific blood glucose reduction-to-insulin unit ratio. Such calculation factors are typically established by a health care provider and communicated to the user of the system 10 so that the user generally has knowledge of these factors and/or sets of factors for various time blocks throughout the day. It will be appreciated that the specific calculation factors display 54 illustrated in FIG. 2C is provided only by way of example, and that the display 54 may alternatively include more or fewer calculation factors requiring user input. In any case, the user may modify any of the information required by the display 54 by selecting appropriate up or down arrows shown on the right side of the display 54. One or more of the calculation factors illustrated in the display 54 may have default values, while others may be reset to zero with each new selection of the display 54.

Figure 2D:
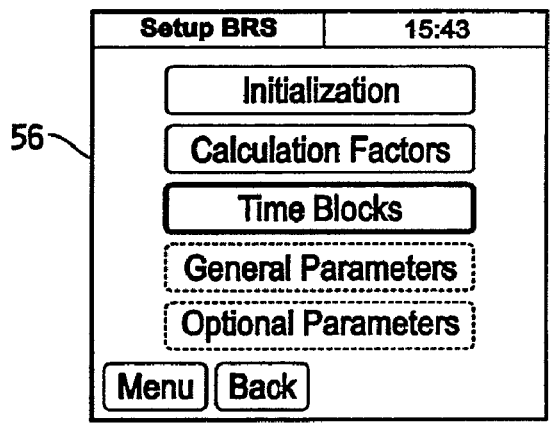

When the user has selected appropriate values for the calculation factors illustrated in display 54, the user selects the "Accept" icon and the "Setup BRS" display 56 shown in FIG. 2D is then produced with the "Time Blocks" feature highlighted. When the user selects the "Time Blocks" feature, the "Time Block Overview" display 58 is produced as shown in FIG. 2E. As long as the "Time Blocks" display 58 is selected, the display 58 displays the words "Time Blocks" in the upper left hand portion of the screen, indicating selection of the Time Blocks set up process. The "Time Block Overview" display 58 allows the user to partition the day into any number, up to six in the illustrated embodiment, of time blocks, wherein the user can then use the display 54 illustrated in FIG. 2C to set up specific upper blood glucose target (BGU), low blood glucose warning (BGL), meal factor (MF) and insulin sensitivity (IS) values for each of the defined time blocks.

When the upper blood glucose target (BGU), low blood glucose warning value (BGL), meal factor (MF), and insulin sensitivity (IS) values have been established for each defined time block through repeated executions of displays 54-58, the "Setup BRS" display 60 illustrated in FIG. 2F is produced wherein the "General Parameters" feature is highlighted. When the user selects the "General Parameters" feature, the "General Parameters" display 62 of FIG. 2G is produced. The display 62 allows the user to enter a high blood glucose warning value (BGH), corresponding to a blood glucose level above which the system 10 displays a high blood glucose warning message to the user as will be described in greater detail hereinafter with respect to FIG. 4D.

When the user has selected an appropriate high blood glucose warning value (BGH), the user selects the "Accept" icon and the "General Parameters" display 64 of FIG. 2H is produced. Display 64 allows the user to select a low blood glucose alert value (BGA), corresponding to a blood glucose level below which the system 10 displays a low blood glucose alert message to the user as will be more fully described herein after with respect to FIG. 4B. When the user has selected a desired low blood glucose alert value (BGA), the user selects the "Accept" icon and the "General Parameters" display 66 if FIG. 2I is produced. After food intake, blood glucose levels will generally increase even if an appropriate insulin bolus was administered prior to or during the meal. The display 66 allows the user to enter a maximum post-prandial blood glucose increase value ($\Delta$PP), corresponding to a maximum post-prandial blood glucose increase above which an additional correction insulin bolus quantity will be determined and recommended by the system 10. When a user has selected an appropriate value for the maximum post-prandial blood glucose increase value ($\Delta$PP), the user selects the "Accept" icon and the "General Parameters" display 68 of FIG. 2J is produced.

The display 68 allows the user to enter a post-prandial lock-out time or duration (TPP), corresponding to a post-prandial time duration in which the rule established by display 66 applies. When a user has selected an appropriate value for the post-prandial lock-out time or duration (TPP), the user selects the "Accept" icon and the "General Parameters" display 70 of FIG. 2K is produced.

The display 70 allows the user to specify a threshold carbohydrate intake (TCI) only above which the rules established by display 66 and 68 apply. After the user has selected an appropriate value for the threshold carbohydrate intake (TCI), the user selects the "Accept" icon and the "General Parameters" display 72 of FIG. 2L is produced.

Repeated insulin bolus corrections for a single, non-meal related blood glucose increase may result in hypoglycemia, and the display 72 accordingly allows the user to select a correction insulin bolus lock-out time or duration (LOT) during which the system 10 will not determine and recommend additional correction insulin boluses based on a single blood glucose elevation event. After selecting an appropriate correction insulin bolus lock-out time or duration (LOT), the user selects the "Accept" icon and the "Setup BRS" display 74 of FIG. 2M is produced. It will be appreciated that the specific "General Parameters" required by displays 62-72 illustrated in FIGS. 2G-2L respectively are provided only by way of example, and that the "General Parameters" displays may alternatively include more or fewer general parameters requiring user input.

The display 74 indicates that the "Calculation Factors," "Time Blocks" and "General Parameters" features have been initialized and that an "Optional Parameters" feature may then be selected. If the user selects the "Optional Parameters" feature, the "Optional Parameters" display 76 of FIG. 2M is produced. The display 76 allows the user to pre-set up a number, e.g., up to three, "Adjustment Levels" for certain activities for which the correction insulin bolus value recommended by the system 10 may be automatically modified. If the user selects the "Yes" icon, a first "Optional Parameters" display 78 for an "Adjustment Level 1/3" is produced as illustrated in FIG. 2P. Within the display 78, the user is permitted to define a first adjustment level and to define an insulin bolus adjustment percentage corresponding to the defined first adjustment level. After the user defines the first adjustment level and accompanying insulin bolus modification percentage at display 78, the user selects the "Accept" icon and another "Optional Parameters" display is produced. For example, FIG. 2Q illustrates a third "Optional Parameters" display 80 for an "Adjustment Level 3/3" in which the user is permitted to define a third adjustment level and corresponding insulin bolus adjustment percentage. In the illustrated example, the user has defined the third adjustment level as a "Driving" level, and has specified a 50% reduction in the recommended correction insulin bolus quantity when the user is undertaking the activity of driving. When the user has appropriately defined and selected the various adjustment levels, this completes the initialization process and the insulin bolus recommendation algorithm is then ready for execution. It will be appreciated that three "Optional Parameters" displays, as well as the specific "Adjustment Level" required by displays 76-80 illustrated in FIGS. 2N and 2P-2Q respectively, are provided only by way of example, and that the "Optional Parameters" displays may alternatively include more, fewer and/or different optional parameters requiring user input.

Those skilled in the art will recognize that the foregoing setup or initialization process illustrated in FIGS. 2A-2N and 2P-2Q represent one example insulin bolus recommendation system initialization or setup procedure, and that steps may be added to, or omitted from, the illustrated procedure without detracting to the scope of the claims appended hereto.

Figure 3A:
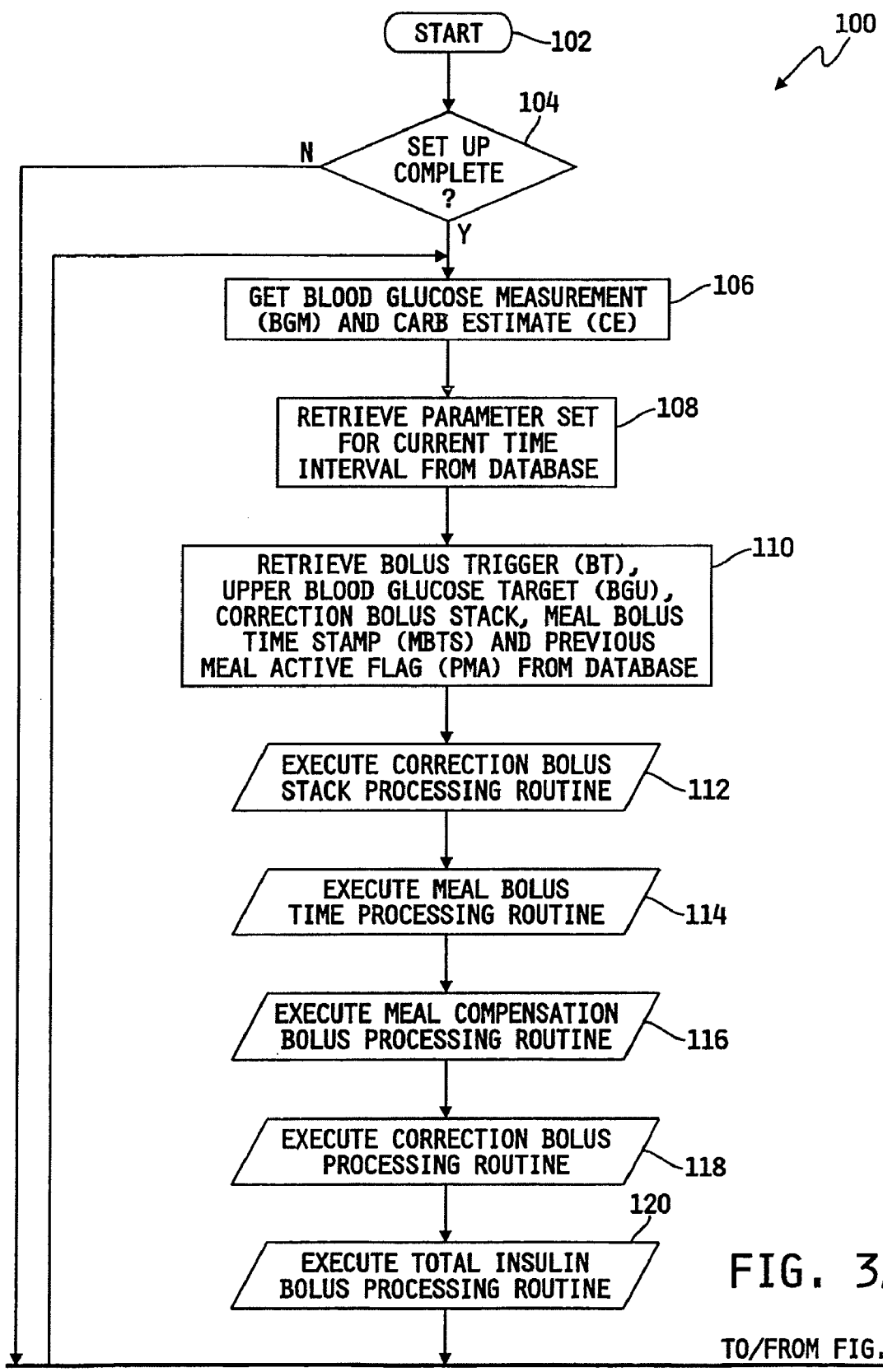
FIGS. 3A and 3B show a flowchart of one illustrative embodiment of an insulin bolus recommendation software algorithm, executable by the system of FIG. 1, for determining and recommending insulin bolus quantities.
Figure 3B:
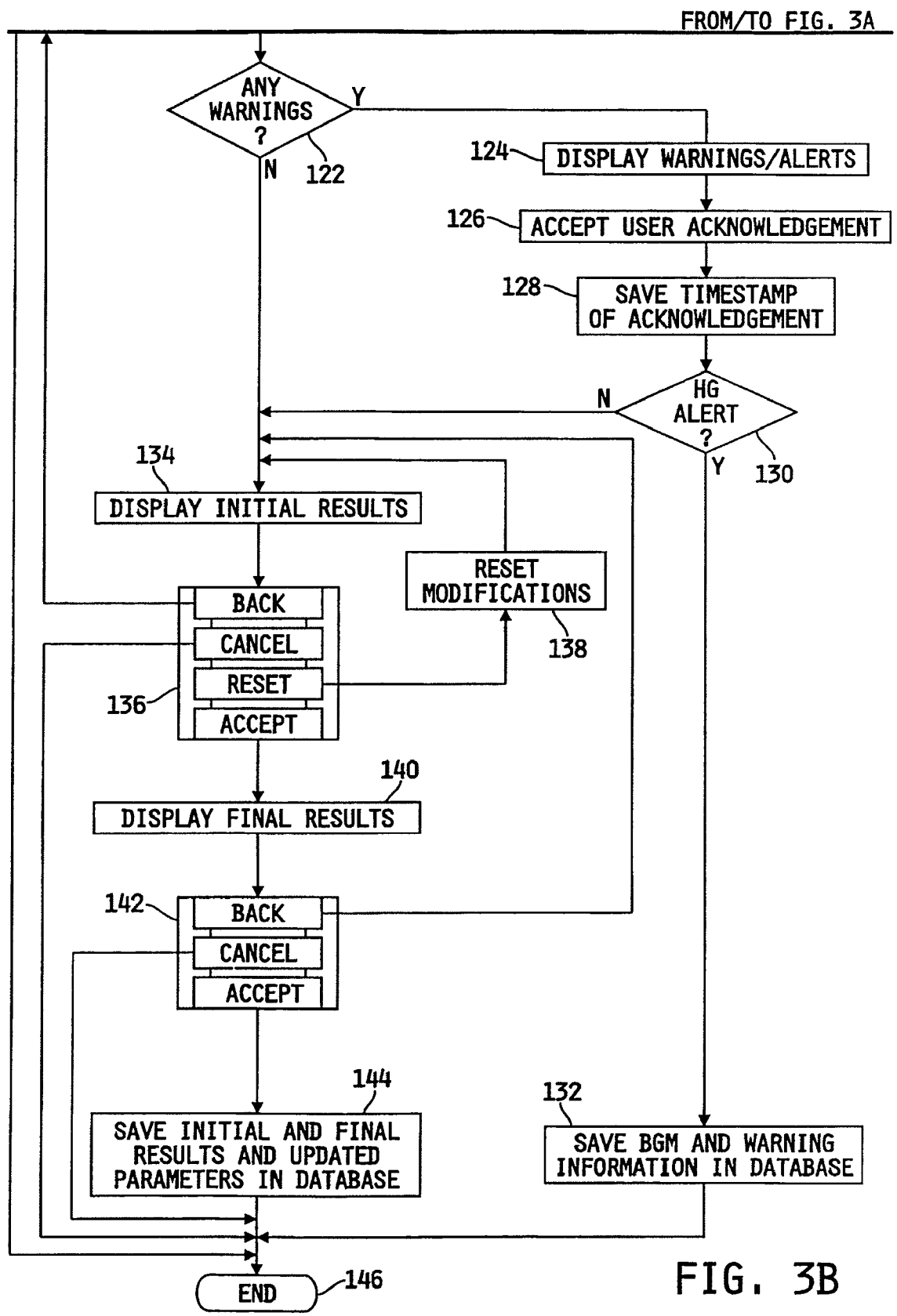

Referring now to FIGS. 3A and 3B, a flow chart of one illustrative embodiment of an insulin bolus recommendation software algorithm 100 for determining and recommending insulin bolus quantities is shown. As with the insulin bolus recommendation system initialization process illustrated in FIGS. 2A-2N and 2P-2Q, the insulin bolus recommendation software algorithm 100 of FIG. 3A will be described as being implemented with the insulin bolus recommendation unit 12 and executed by the control circuit 14, wherein the insulin bolus recommendation unit 12 is provided in the form of a conventional PDA or a hand-held, application-specific insulin bolus recommendation unit, although those skilled in the art will recognize that the algorithm 100 may alternatively be implemented with the bolus recommendation unit 12 and/or bolus recommendation unit 30 provided in any one or more of the physical forms described hereinabove.

Figure 4A:
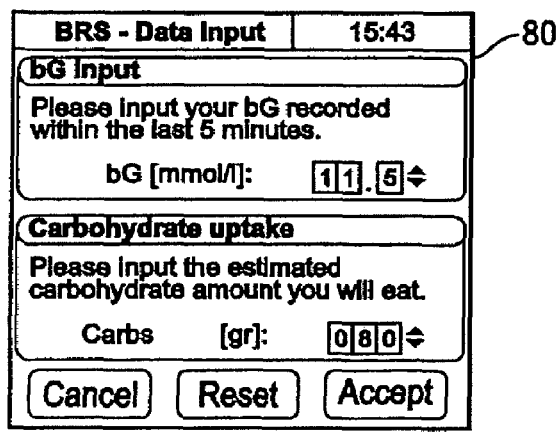
FIG. 4A is an interactive display screen illustrating one embodiment of a graphical user interface for executing step 106 of the software algorithm of FIG. 3.
Figure 4B:
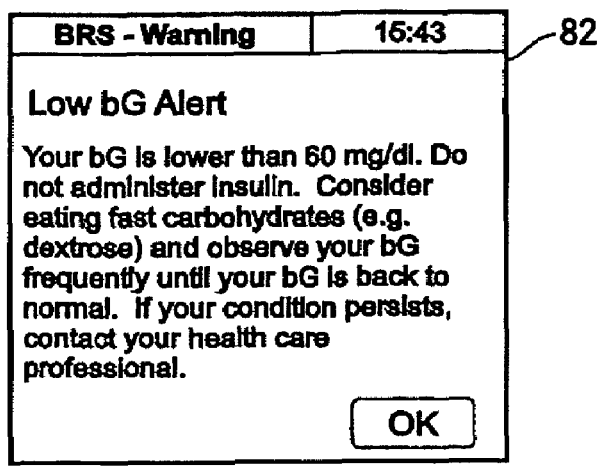
FIG. 4B is an interactive display screen illustrating one embodiment of a graphical user interface for executing steps 124-126 of the software algorithm of FIG. 3.
Figure 4C:
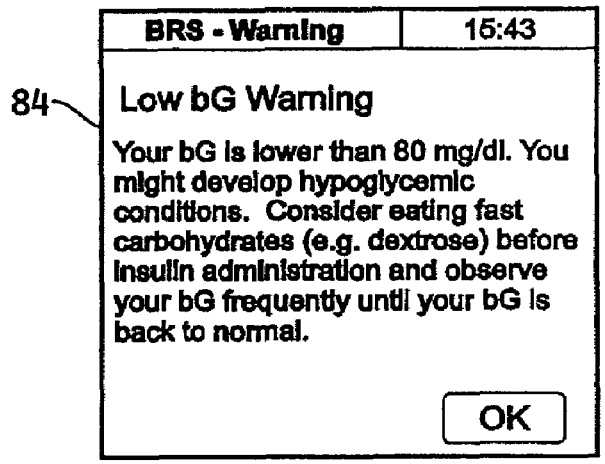
FIG. 4C is an interactive display screen illustrating one embodiment of another graphical user interface for executing steps 124-126 of the software algorithm of FIG. 3.
Figure 4D:
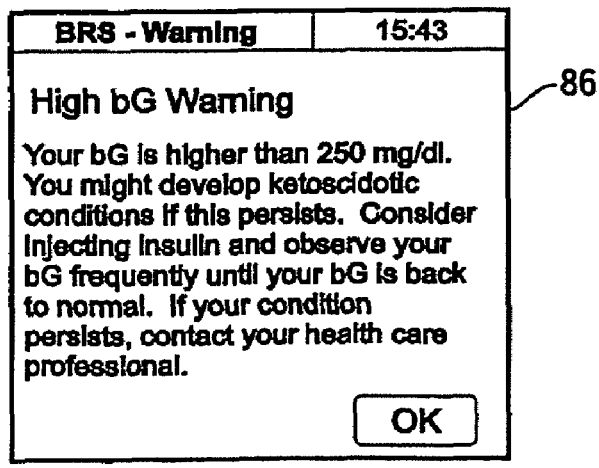
FIG. 4D is an interactive display screen illustrating one embodiment of yet another graphical user interface for executing steps 124-126 of the software algorithm of FIG. 3.

In any case, the algorithm 100 begins at step 102 and at step 104 the control circuit 14 determines whether the set up process, e.g., the insulin bolus recommendation system initialization or setup process illustrated in FIGS. 2A-2N and 2P-2Q, is complete. If not, execution of the algorithm 100 advances to step 146 where the algorithm 100 is terminated. If, on the other hand, the control circuit 14 determines at step 104 that the set up process is complete, algorithm execution advances to step 106 where the control circuit 14 is operable to obtain a blood glucose measurement (BGM) and a carbohydrate estimate (CE). Referring to FIG. 4A, an interactive display 80 is shown illustrating one embodiment of a graphical user interface displayed on the display unit 16 of the insulin bolus recommendation unit 12 for executing step 106 of the algorithm 100. The display 80 illustrated in FIG. 4A prompts the user to enter a blood glucose measurement value (BGM) corresponding to the user's blood glucose level that was measured within some time frame, e.g., five minutes, of entering the blood glucose measurement data into the algorithm 100. The user may obtain the blood glucose measurement value, BGM, via any conventional blood glucose measurement device and/or technique. Alternatively, an automatic blood glucose determination unit of the type described hereinabove may determine the user's blood glucose value at step 106 and provide the corresponding blood glucose measurement value, BGM, directly to the algorithm 100. In any case, the display 80 also prompts the user to enter a carbohydrate estimate (CE) corresponding to a quantity of carbohydrates that will be consumed in a subsequent meal or snack. After the user enters the measured blood glucose level (BGM), and a carbohydrate estimate (CE), if any, the user selects the "Accept" icon and execution of the algorithm 100 advances from step 106 to step 108 where the control circuit 14 is operable to retrieve the setup parameters for the current time interval from an insulin bolus recommendation database stored in the memory unit 20. The insulin bolus recommendation database will typically include at least the initialization or setup parameters described hereinabove with respect to FIGS. 2A-2N and 2P-2Q, as well as information relating to previous blood glucose measurements, previously recommended insulin boluses, lock-out timer values, and the like.

From step 108, execution of the algorithm 100 advances to step 110 where the control circuit 14 is operable to retrieve from the memory unit 20 current values of a bolus trigger (BT), the upper blood glucose target (BGU), a correction bolus stack, a meal bolus time stamp (MBTS) and a previous meal active flag (PMA). In the first execution of the algorithm 100, the bolus trigger (BT) will be set equal to the upper blood glucose target (BGU), the meal bolus time stamp (MBTS) will be zero, the previous meal active flag (PMA) will be "false" and the correction bolus stack will be empty. Any one or more of these values may change, and the correction bolus stack may become populated with correction bolus information, as the execution of the algorithm 100 advances and/or through repeated executions of the algorithm 100 as will become more apparent from the following detailed description of the remainder of the algorithm 100.

Figure 5:
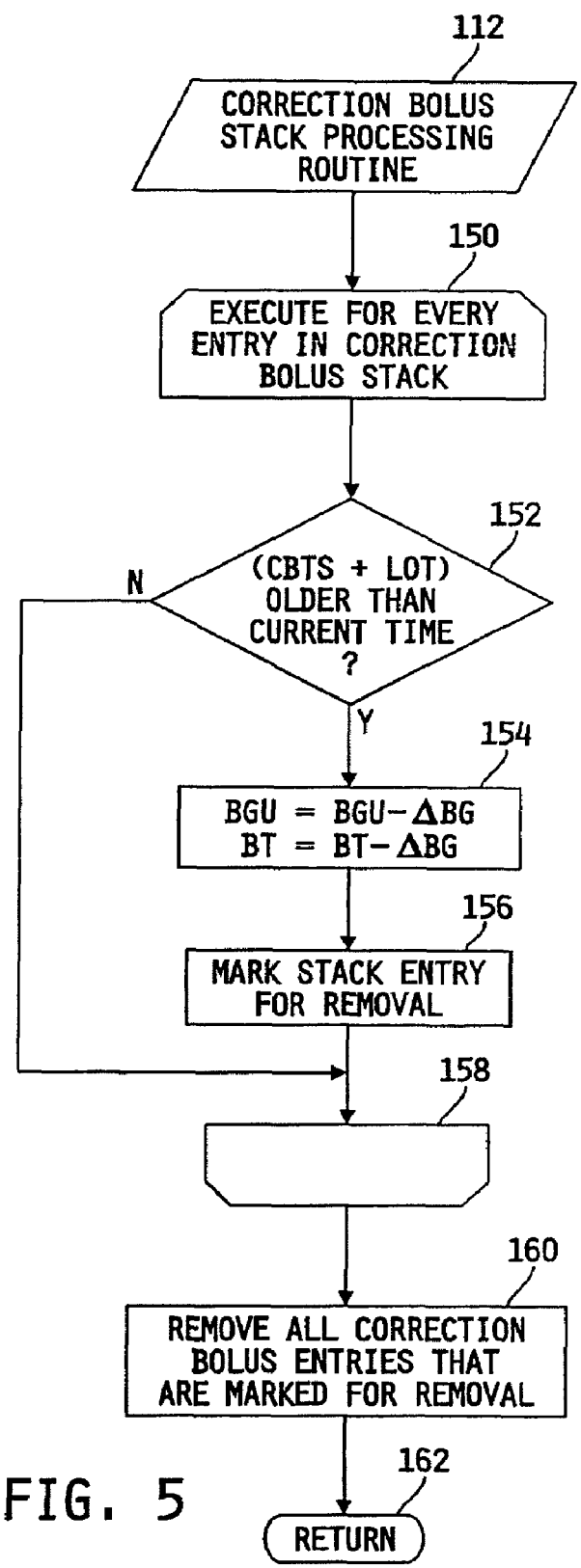
FIG. 5 is a flowchart of one illustrative embodiment of a software routine for executing step 112 of FIG. 3.

Execution of the algorithm 100 advances from step 110 to step 112 where the control circuit 14 is operable to execute a correction bolus stack processing routine. Referring to FIG. 5, a flow chart of one illustrative embodiment of the collection bolus stack processing routine called by step 112 of the algorithm 100 is shown. In the illustrated embodiment, the correction bolus stack processing routine 112 begins at step 150 where the control circuit 14 is operable to execute each of the steps 152-156 between steps 150 and 158 for every entry in the correction bolus stack. In at least the first execution of the algorithm 100, as described hereinabove, the correction bolus stack will be empty, and the routine 112 will accordingly advance directly to step 162 which returns execution of the routine 112 back to algorithm 100.

Each time a correction insulin bolus quantity is determined and recommended by the insulin bolus recommendation system 10 under the direction of the software algorithm 100, the control circuit 14 is operable to establish a correction bolus time stamp (CBTS), corresponding to the actual time at which the correction insulin bolus quantity was determined, recommended and/or presumably administered to the user. Thereafter, the insulin bolus recommendation system 10 is "locked out" from determining and recommending further insulin bolus quantities relating to the blood glucose increase for which the correction insulin bolus quantity was recommended (and presumably administered) at time CBTS for the correction insulin bolus lock-out time period, LOT. As will be described in greater detail hereinafter with respect to FIG. 8, the insulin bolus recommendation system 10 is operable to effectuate this "lock-out" feature by increasing the upper blood glucose target (BGU) by a computed blood glucose quantity (ΔBG). Thus, each entry in the correction bolus stack will have a correction bolus time stamp, CBTS, and a blood glucose increase value, ΔBG, associated with it.

At step 152, the control circuit 14 is operable to compare the sum of the correction bolus time stamp, CBTS and the correction insulin bolus lock-out time period, LOT, to the current time for one of the entries in the correction bolus stack. If the sum of CBTS and LOT for the selected entry is older than the current time, the associated ΔBG for that stack entry is subtracted from the current value of the upper blood glucose target, BGU, and also from the current value of the bolus trigger, BT, and that entire stack entry is then marked for deletion or removal. After all entries in the correction bolus stack are similarly processed, execution of the routine 112 advances to step 160 where all of the correction bolus entries in the correction bolus stack that are marked for removal are removed or deleted from the correction bolus stack. Thereafter at step 162, execution of the routine 112 is returned to step 112 of the algorithm 100.

It will be appreciated that the correction bolus stack processing routine illustrated in FIG. 5 is provided only by way of example, and that the routine of FIG. 5 may alternatively be configured to process the collection of correction bolus stack entries according to other known software techniques. As one example, the collection of correction bolus time stamps, CBTS, and associated blood glucose increase values, ΔBG, may be entered, as they occur, into a conventional queue. The routine of FIG. 5 may then be configured to process not every entry in the correction bolus queue, but only the oldest queue entries for which CBTS+LOT is older than the current time. Those skilled in the art will recognize other software techniques for processing the collection of correction bolus time stamps, CBTS, and associated blood glucose increase values, ΔBG, in the manner just described, and any such alternate data processing techniques are intended to fall within the scope of the claims appended hereto.

Figure 6:
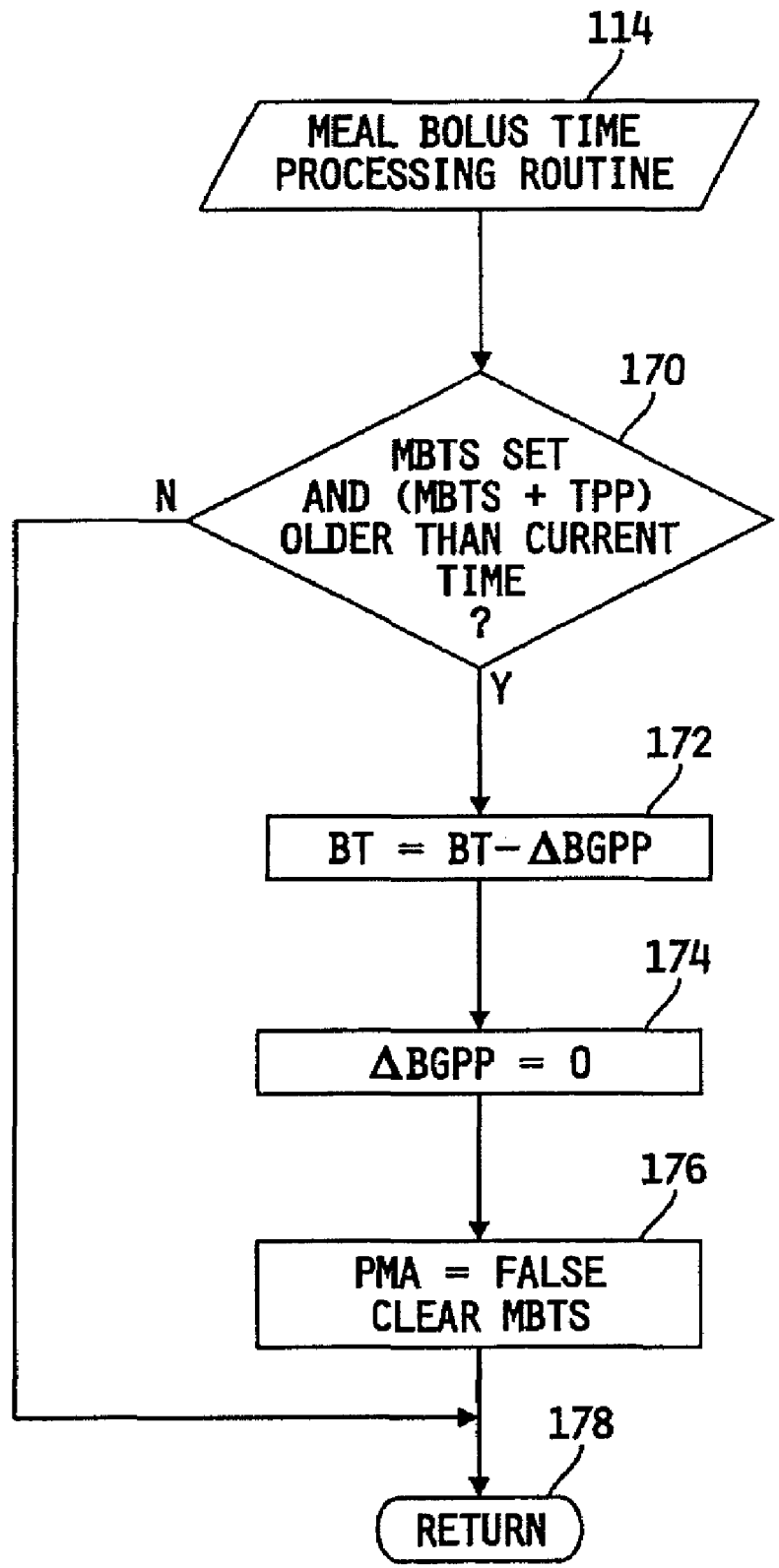
FIG. 6 is a flowchart of one illustrative embodiment of a software routine for executing step 114 of FIG. 3.

Following the completion of step 112, execution of the algorithm 100 advances to step 114 where the control circuit 14 is operable to execute a meal bolus time processing routine. Referring now to FIG. 6, a flow chart of one illustrative embodiment of the meal bolus time processing routine called by step 114 of the algorithm 100 is shown. If a meal compensation insulin bolus quantity is determined and recommended by the insulin bolus recommendation system 10 under the direction of the software algorithm 100, the control circuit 14 is operable to establish a meal bolus time stamp (MBTS), corresponding to the actual time at which the meal compensation insulin bolus quantity was determined, recommended and/or presumably administered to the user. Thereafter, the insulin bolus recommendation system 10 is "locked out" from determining and recommending further insulin bolus quantities relating to post-prandial blood glucose increases for the post-prandial lock-out time period, TPP. As will be described in greater detail hereinafter with respect to FIG. 8, the insulin bolus recommendation system 10 is operable to effectuate this post-prandial "lock-out" feature by increasing the upper blood glucose target (BGU) by a computed post-prandial blood glucose increase value (ΔBGPP).

In the illustrated embodiment, the meal bolus time processing routine begins at step 170 where the control circuit 14 is operable to determine whether the meal bolus time stamp, MBTS is set, and if so whether the sum of the meal bolus time stamp, MBTS, and the post-prandial lock-out time period, TPP, is older than the current time. If so, the control circuit 14 is operable at step 172 to subtract the post-prandial blood glucose increase value, ΔBGPP, from the current value of the bolus trigger, BT, and then at step 174 to set the post-prandial blood glucose increase value, ΔBGPP, equal to zero. Thereafter at step 176, the control circuit 14 is operable to set the previous meal active flag, PMA, equal to "false", and then to clear the meal bolus time stamp, MBTS, e.g., by setting MBTS=zero. Execution of the meal bolus time processing routine advances from step 176, and from the "N" branch of step 170 to step 178 where execution of the meal bolus time processing routine is returned to step 114 to the algorithm 100.

Figure 7:
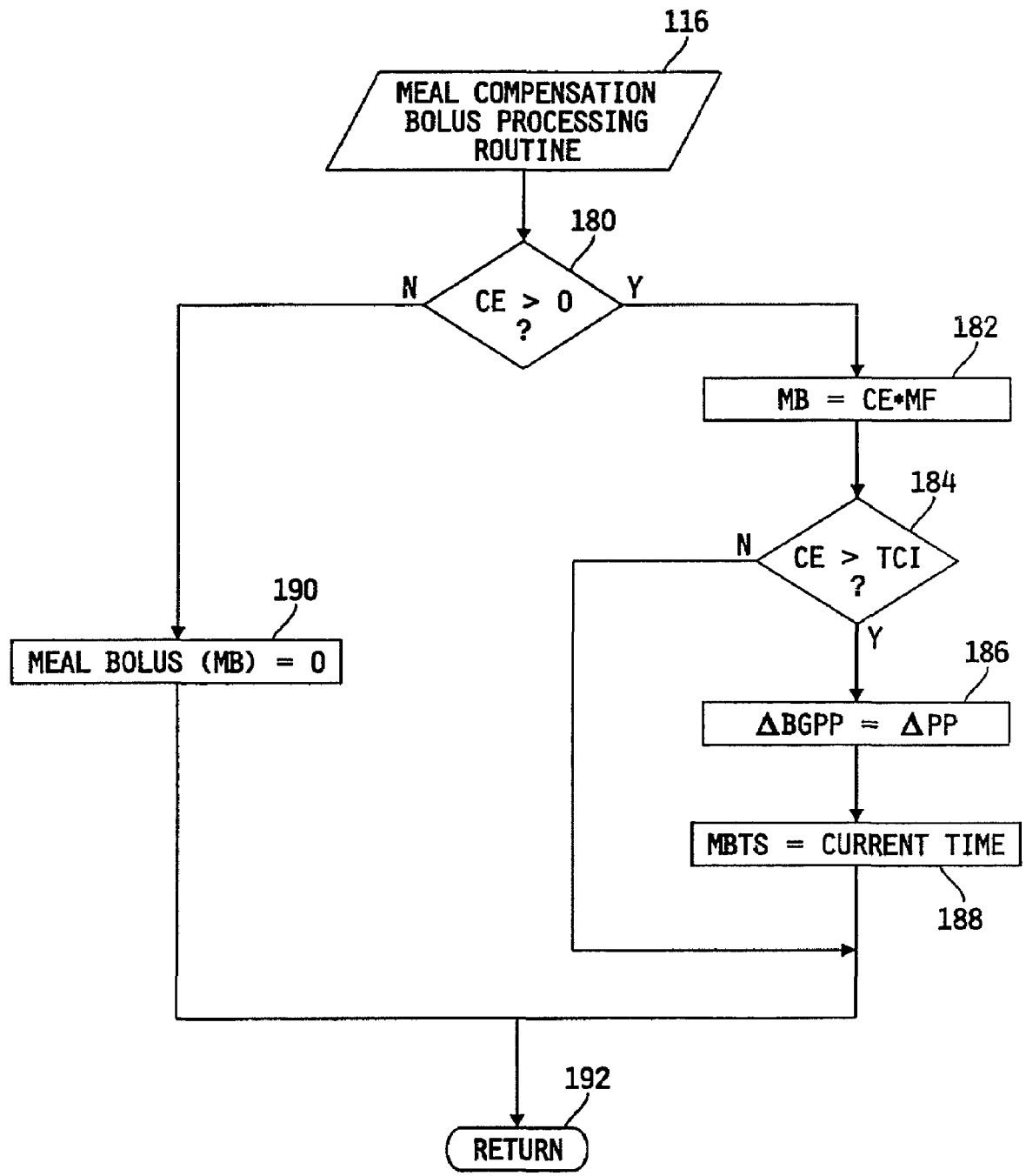
FIG. 7 is a flowchart of one illustrative embodiment of a software routine for executing step 116 of FIG. 3.

Following the completion of step 114, execution of the algorithm 100 advances to step 116 where the control circuit 14 is operable to execute a meal compensation bolus processing routine. Referring now to FIG. 7, a flow chart of one illustrative embodiment of the meal compensation bolus processing routine called by step 116 of the algorithm 100 is shown. In the illustrated embodiment, the meal compensation bolus processing routine begins at step 180 where the control circuit 14 is operable to determine whether the carbohydrate estimate (CE) established at step 106 of the algorithm 100 is greater than zero. If so, execution of the routine advances to step 182 where the control circuit 14 is operable to compute a recommended meal compensation insulin bolus quantity, MB, as the product of the carbohydrate estimate, CE, and the meal factor, MF. Thereafter at step 184, the control circuit 14 is operable to determine whether the carbohydrate estimate, CE, is greater than the threshold carbohydrate intake, TCI, established as part of the set up or initialization procedure described hereinabove with respect to FIGS. 2A-2N and 2P-2Q. If so, execution of the routine advances to step 186 where the control circuit 14 is operable to set the post-prandial blood glucose increase value, ΔBGPP, equal to the maximum post-prandial blood glucose increase value, ΔPP, established as part of the set up or initialization procedure described hereinabove with respect to FIGS. 2A-2N and 2P-2Q. Thereafter at step 188, the control circuit is operable to set the meal bolus time stamp, MBTS, equal to the current time period. If, at step 180, the control circuit 14 determines that the carbohydrate estimate, CE, is not greater than zero, the control circuit 14 is operable to set the meal compensation insulin bolus quantity, MB, equal to zero. Execution of the routine advances from steps 188 and 190 as well as from the "N" branch of step 184, to step 192 where execution of the meal compensation bolus processing routine is returned to step 116 of the algorithm 100.

Figure 8A:
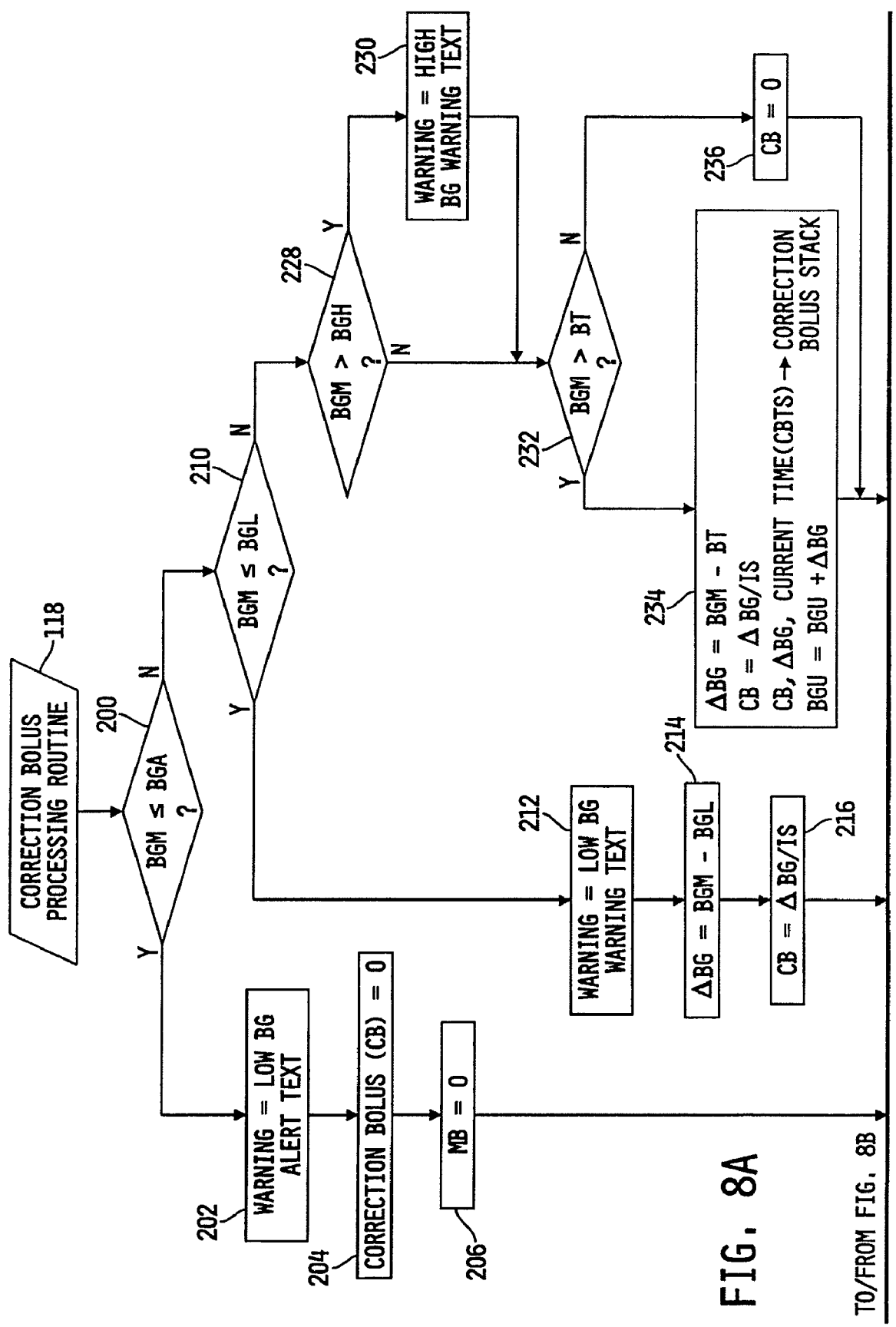
FIGS. 8A and 8B show a flowchart of one illustrative embodiment of a software routine for executing step 118 of FIG. 3.
Figure 8B:
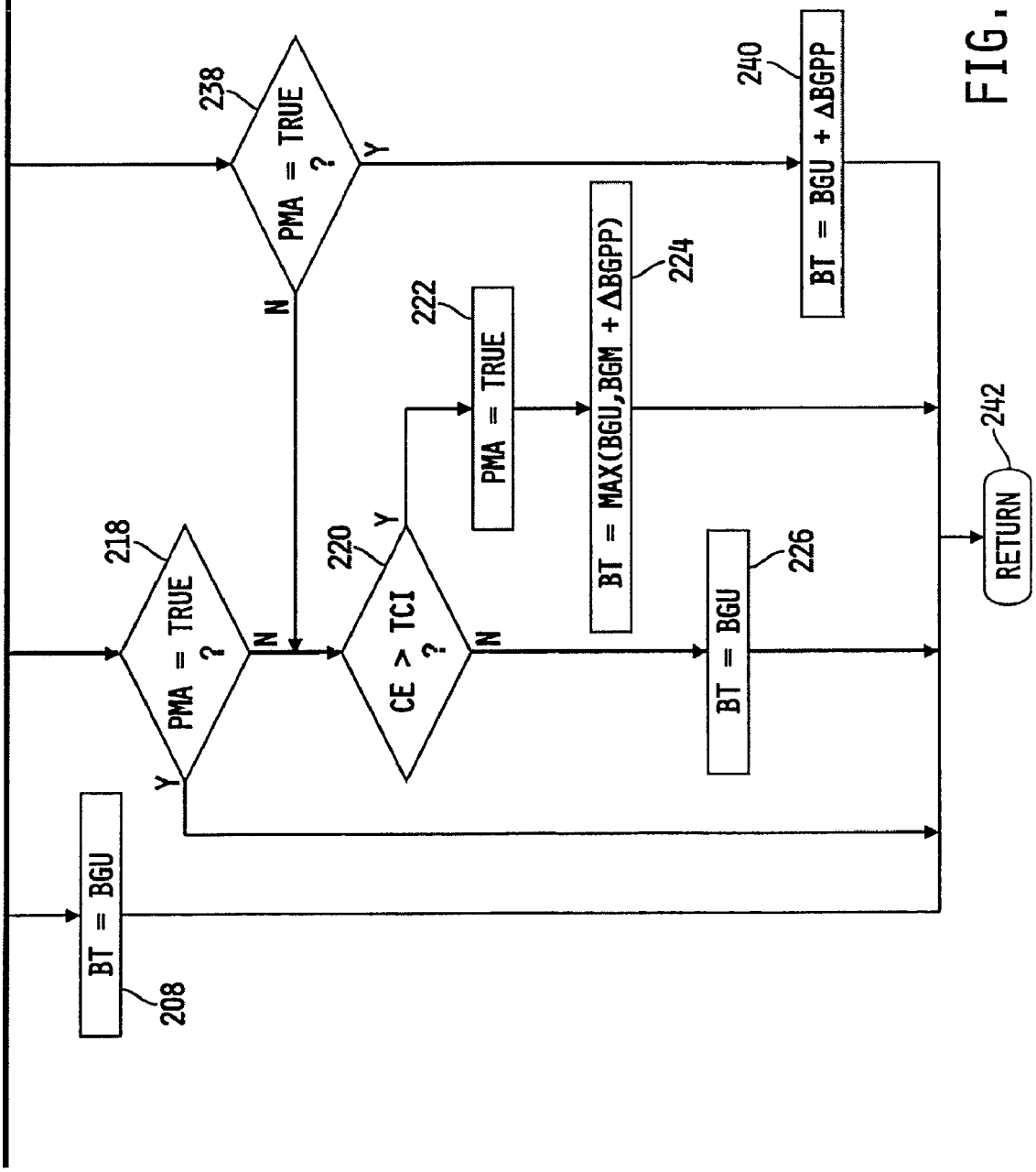

Following the completion of step 116, execution of the algorithm 100 advances to step 118 where the control circuit 14 is operable to execute a correction bolus processing routine. Referring now to FIGS. 8A and 8B, a flow chart of one illustrative embodiment of a correction bolus processing routine called by step 118 of the algorithm 100 is shown. In the illustrated embodiment, the correction bolus processing routine begins at step 200 where the control circuit 14 is operable to compare the measured blood glucose value, BGM, which was determined at step 106 of the algorithm 100, to the low blood glucose alert value, BGA, established as part of the set up or initialization procedure described hereinabove with respect to FIGS. 2A-2N and 2P-2Q. If the control circuit 14 determines at step 200 that BGM is less or equal to BGA, execution of the routine advances to step 202 where the control circuit 14 selects as a warning the low blood glucose alert message illustrated by example in the display 82 of FIG. 4B. Thereafter at step 204, the control circuit 14 is operable to set a correction insulin bolus quantity, CB, to zero, and then at step 206 to set the meal compensation insulin bolus quantity, MB, equal to zero. Following step 206, execution of the correction bolus processing routine advances to step 208 where the control circuit 14 is operable to set the bolus trigger, BT, to the upper blood glucose target, BGU.

If, at step 200, the control circuit 14 determines that the measured blood glucose value, BGM, is greater than the low blood glucose alert value, BGA, execution of the correction bolus processing routine advances to step 210 where the control circuit 14 is operable to compare the measured blood glucose value, BGM, to the low blood glucose warning value, BGL. If, at step 210, the control circuit 14 determines that BGM is less than or equal to BGL, execution of the correction bolus routine advances to step 212 where the control circuit 14 sets as a warning the low blood glucose warning message illustrated by example in the display 84 of FIG. 4C. Thereafter at step 214, the control circuit 14 is operable to compute the blood glucose increase value, ΔBG, as the measured blood glucose value, BGM, minus the low blood glucose warning value, BGL. Thereafter at step 216, the circuit 14 is operable to compute the correction insulin bolus quantity, CB, as the ratio of ΔBG and the insulin sensitivity value, IS, established as part of the set up or initialization procedure described hereinabove with respect to FIGS. 2A-2N and 2P-2Q.

Following step 216, the correction bolus processing routine advances to step 218 where the control circuit 14 is operable to determine the status of the previous meal active flag, PMA. If, at step 218, the control circuit 14 determines that the previous meal active flag, PMA, is not "true", execution of the routine advances to step 220 where the control circuit 14 is operable to determine whether the carbohydrate estimate, CE, is greater than the threshold carbohydrate intake, TCI, established as part of the set up or initialization procedure described hereinabove with respect to FIGS. 2A-2N and 2P-2Q. If so, the control circuit 14 is operable at step 222 to set the previous meal active flag, PMA, to "true", and thereafter at step 224 to set the bolus trigger, BT, to the maximum of the upper blood glucose target, BGU, and the sum of the measured blood glucose value, BGM, and the post-prandial blood glucose increase value, ΔBGPP. If, on the other hand, the control circuit 14 determines at step 220 that the carbohydrate estimate, CE, is not greater than the threshold carbohydrate intake, TCI, execution of the routine advances to step 226 where control circuit 14 is operable to set the bolus trigger, BT, to the upper blood glucose target, BGU.

If, at step 210, the control circuit 14 determines that the measured blood glucose value, BGM, is greater than the low blood glucose warning value, BGL, execution of the correction bolus processing routine advances to step 228 where the control circuit 14 is operable to determine whether the measured blood glucose value, BGM, is greater than the high blood glucose warning value, BGH. If so, the control circuit 14 selects as a warning at step 230 the high blood glucose warning message illustrated by example in the display 86 of FIG. 4D. From step 230, and from the "N" branch of step 228, execution of the correction bolus processing routine advances to step 232 where the control circuit 14 is operable to compare the measured blood glucose value, BGM, to the current value of the bolus trigger, BT. If, at step 232, control circuit 14 determines that BGM is greater than BT, execution of the routine advances to step 234.

At step 234, the control circuit 14 is operable to set the blood glucose increase value, ΔBG, equal to the measured blood glucose value, BGM, minus the current value of the bolus trigger, BT. The control circuit 14 is also operable at step 234 to compute the correction insulin bolus quantity, CB, as the ratio of the blood glucose increase value, ΔBG, and the insulin sensitivity value, IS. The control circuit 14 is further operable at step 234 to enter the current time in the form of a correction bolus time stamp, CBTS, and the current blood glucose increase value, ΔBG, into the correction bolus stack as described hereinabove with respect to FIG. 5. Finally, the control circuit is operable at step 234 to set the upper glucose target, BGU, to the sum of the current upper blood glucose target, BGU, and the blood glucose increase value, ΔBG. If, at step 232, the control circuit 14 determines that the measures blood glucose value, BGM, is not greater than the current value of the bolus trigger, BT, execution of the routine advances to step 236 where the control circuit 14 is operable to set the correction insulin bolus quantity, CB, equal to zero.

Following either of steps 234 and 236, execution of the correction insulin bolus processing routine advances to step 238 where the control circuit 14 is operable to determine the status of the previous meal active flag, PMA. If the control circuit 14 determines at step 238 that the previous meal active flag, PMA, is "true", execution of the routine advances to step 240 where the control circuit 14 is operable to compute a current value of the bolus trigger, BT, as the sum of the upper blood glucose target, BGU, and the post-prandial blood glucose increase value, ΔBGPP. If, on the other hand, the control circuit 14 determines at step 238 that the previous meal active flag, PMA, is not "true", execution of the routine advances to step 220. Steps 208, 226 and 240 as well as the "Y" branch of step 218, advance to step 242 where execution of the correction bolus processing routine is returned to step 118 of the algorithm 100.

Figure 9:
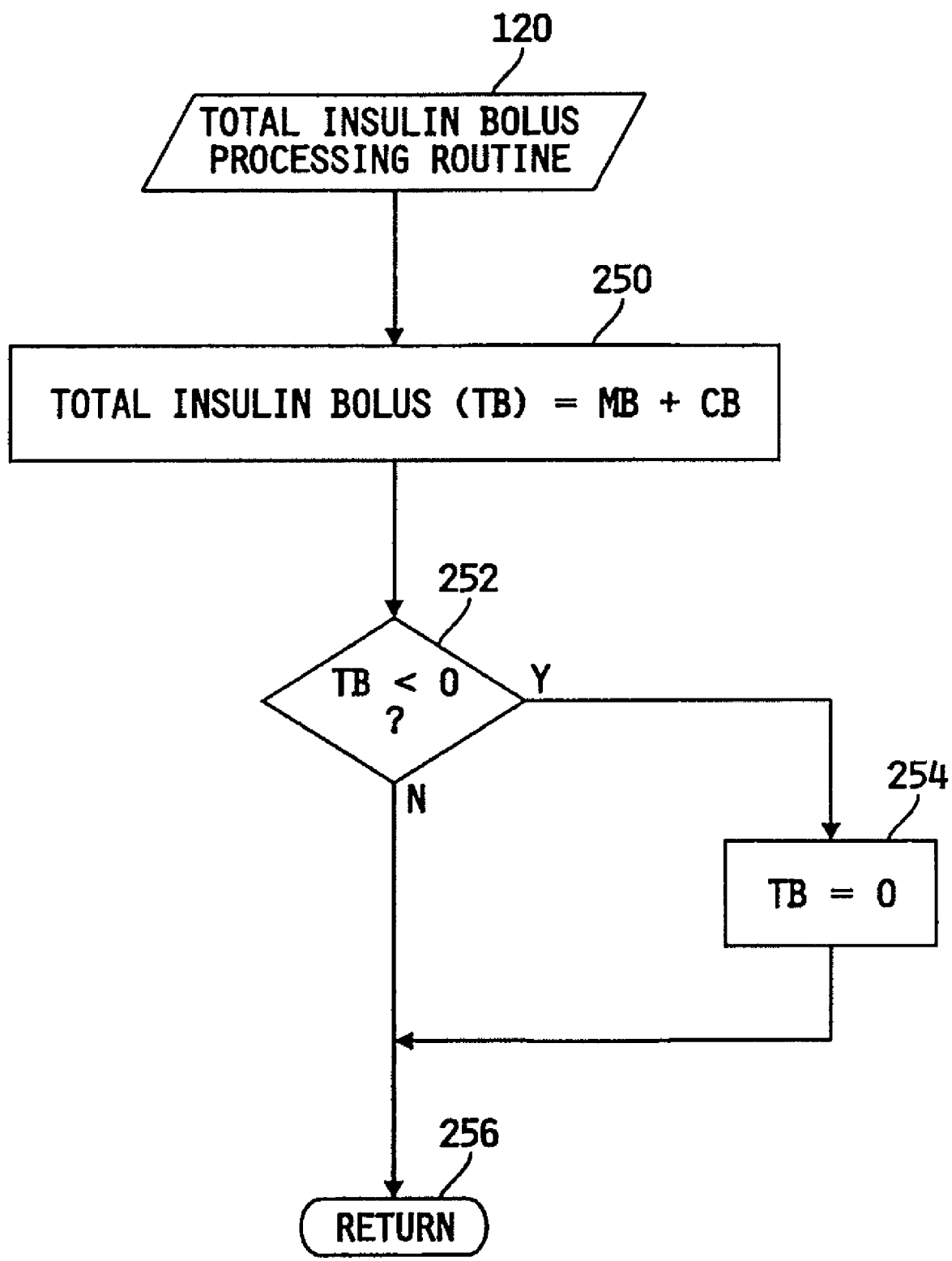
FIG. 9 is a flowchart of one illustrative embodiment of a software routine for executing step 120 of FIG. 3.

Following the completion of step 118, execution of the algorithm 100 advances to step 120 where the control circuit 14 is operable to execute a total insulin bolus processing routine. Referring now to FIG. 9, a flow chart of one illustrative embodiment of the total insulin bolus processing routine called by step 120 of the algorithm 100 is shown. In the illustrated embodiment, the total insulin bolus processing routine begins at step 250 where the control circuit 14 is operable to compute a total insulin bolus quantity, TB, as the sum of the meal compensation insulin bolus quantity, MB, and the correction insulin bolus quantity, CB. Thereafter at step 252, the control circuit 14 is operable to determine whether the total insulin bolus quantity, TB, is less than zero. If so, execution of the routine advances to step 254 where the control circuit 14 is operable to set the total insulin bolus quantity, TB, equal to zero. Execution of the total insulin bolus processing routine advances from step 254, and also from the "N" branch of step 252, to step 256 where execution of the total insulin bolus processing routine is returned to step 120 of the algorithm 100.

Algorithm 100 advances from step 120 to step 122 where the control circuit 14 is operable to determine whether any warnings or alerts have been selected for display by the correction bolus processing routine called by step 118 of the algorithm 100. If so, execution of the algorithm 100 advances to step 124 where the control circuit 14 is operable to display the selected warning or alert as illustrated by the various example warning and alert messages shown in FIGS. 4B-4D. Each one of the warning or alert message displays 82, 84 and 86 includes an "OK" icon which the user selects at step 126 of the algorithm 100 to acknowledge the alert or warning. Thereafter at step 128, the control circuit 14 saves in the memory unit 20 the time stamp of the warning or alert acknowledgement. Thereafter at step 130, the control circuit 14 is operable to determine whether the warning displayed at step 124 corresponds to the low blood glucose, or hypoglycemia, alert illustrated in the display 82 of FIG. 4B. If so, execution of the algorithm 100 advances to step 132 where the control circuit 14 is operable to save the measured blood glucose value, BGM, and the accompanying warning or alert information in the database stored within the memory unit 20.

Figures 4E, 4F, 10:
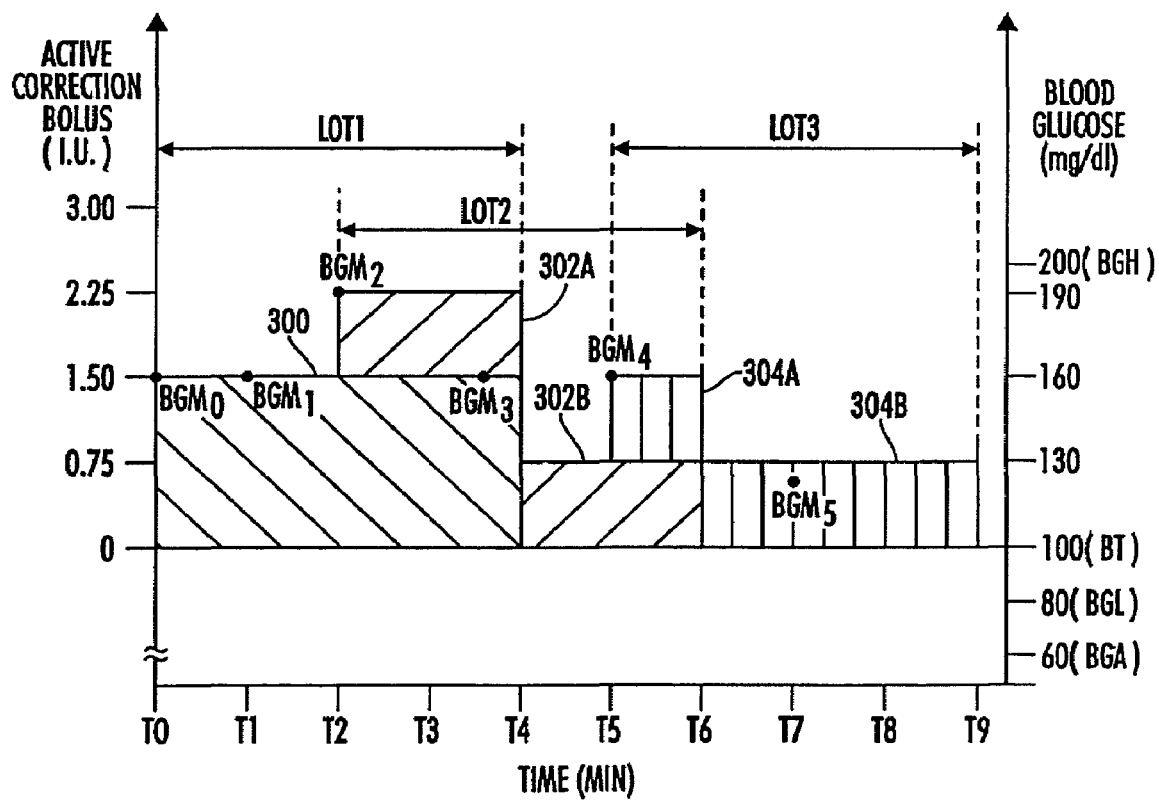
FIG. 4E is an interactive display screen illustrating one embodiment of a graphical user interface for executing step 134 of the software algorithm of FIG. 3.
FIG. 4F is an interactive display screen illustrating one embodiment of a graphical user interface for executing step 140 of the software algorithm of FIG. 3.
FIG. 10 is a plot of blood glucose and active correction bolus vs. time illustrating one example of the operation of the insulin bolus recommendation algorithm of FIG. 3.

If, on the other hand, the control circuit 14 determines at step 130 that the warning message displayed at step 124 does not correspond to the low blood glucose, or hypoglycemia, alert, execution of the algorithm 100 advances to step 134 where control circuit 14 is operable to display the initial insulin bolus recommendation results computed by the control circuit 14. Referring to FIG. 4E, an interactive display 88 is shown illustrating one embodiment of a graphical user interface displayed on the display unit 16 of the insulin bolus recommendation unit 12 for executing step 134 of the algorithm 100. In the graphical display 88 illustrated in FIG. 4E, a total insulin bolus recommendation of 11.4 units is shown as the sum of a recommended 10.4 units of a computed meal compensation insulin bolus quantity, MB, and a one unit recommendation of a computed correction insulin bolus quantity, CB. Also shown in the display 88 is an adjustment selection area allowing the user to select any one or more of the predefined insulin bolus modifying adjustment levels 1-3 established as part of the set up or initialization procedure described hereinabove with respect to FIGS. 2A-2N and 2P-2Q. In the example illustrated in FIG. 4E, the third level, corresponding to a 50% insulin bolus reduction for a "driving activity" is shown as being selected.

Following step 134 of the algorithm 100, the user is offered at step 136, as illustrated graphically in FIG. 4E, options to "Cancel", "Back", "Reset" and "Accept" the initial results displayed in FIG. 4E. If the user selects the "Cancel" icon, the algorithm 100 advances to step 146 where the algorithm 100 is terminated. If instead the user selects "Back," execution of the algorithm 100 loops back to step 106 to prompt the user for new blood glucose and estimated carbohydrate information. If instead the user selects "Reset," the algorithm 100 advances to step 138 where the control circuit 14 is operable to reset any modifications that the user has made to the information shown in the display 88, and then to re-display the original initial results at step 134. After the user has modified the "Adjustments" information as desired, the user selects the "Accept," and the algorithm 100 advances to step 140 where the control circuit 14 is operable to display the final insulin bolus recommendation results as illustrated by example in the display 90 of FIG. 4F.

In the graphical display 90 illustrated in FIG. 4F, a total insulin bolus recommendation of 5.7 international units is shown as the sum of a recommended 10.4 international units of a computed meal compensation insulin bolus quantity, MB, and a one international unit recommendation of a computed correction insulin bolus quantity, CB, less the "driving" adjustment percentage. Following step 140 of the algorithm 100, the user is offered at step 142, as illustrated graphically in FIG. 4F, options to "Cancel", "Back" and "Accept" the final results displayed in FIG. 4F. If the user selects the "Cancel" icon, the algorithm 100 advances to step 146 where the algorithm 100 is terminated. If instead the user selects "Back," execution of the algorithm 100 loops back to step 134 where the control circuit 14 is operable to again display the initial results. By selecting the "Accept" icon, the user acknowledges that the recommended insulin dosage displayed in the display 90 will be administered to the user, and that the current dataset will be transferred to the database in the memory unit 20. Execution of the algorithm advances from the "Accept" option of step 142 to step 144 where the control circuit is accordingly operable to save the current dataset, including the initial and final results, as well as the updated operating parameters, into the database stored in the memory unit 20. Execution of the algorithm 100 then advances from step 144 to step 146 where the algorithm 100 is terminated.

EXAMPLE 1

With the aid of FIG. 10, one example of the operation of the algorithm 100 will now be provided. In this example, no meals or snacks will be ingested during the illustrated time frame, and consequently no meal compensation insulin bolus will be computed or recommended. This example presumes that the initialization or set up process illustrated in FIGS. 2A-2N and 2P-2Q has previously been executed, resulting in the example calculation factors, general parameters and optional parameters applicable during the illustrated time frame and shown in the following Table 1:

TABLE 1

| FACTOR OR PARAMETER | VALUE |
| --- | --- |
| BGU | 100 mg/dl |
| BGA | 60 mg/dl |
| BGL | 80 mg/dl |
| BGH | 200 mg/dl |
| MF | 1.0 I.U./10 gr. carbohydrates |
| IS | 40 mg/dl/I.U. |
| $\Delta$PP | 50 mg/dl |
| TCI | 10 gr |
| TPP | 150 min |
| LOT | 120 min |
| Adjustment Level 1/3 | 0% |
| Adjustment Level 2/3 | 0% |
| Adjustment Level 3/3 | 0% |

Referring now to FIG. 10, a plot of blood glucose and active correction bolus vs. time illustrating this example is shown. With the set up complete, the algorithm 100 prompts the user at step 106 to input a current blood glucose measurement, BGM, and a carbohydrate estimate, CE. At time T0, the user obtains a blood glucose measurement, $BGM_0$, and accordingly enters in the display 80 a BGM of 160 mg/dl. Since no meals or snacks will be ingested during the time interval illustrated in FIG. 10, the user also enters in the display 80 a CE of 0 gr. Alternatively, the display 80 may have CE=0 as a default value, in which case the user need only accept CE=0 gr. step 106. Thereafter at step 108, the control circuit 14 retrieves the parameter set, corresponding to the information in Table 1, from the database stored in the memory unit 20. At step 110, the control circuit 14 also retrieves current values of the bolus trigger, BT, the upper blood glucose target, BGU, the meal bolus time stamp, MBTS, and the previous meal active flag, PMA, as well as the correction bolus stack. For the first execution of the algorithm 100, BT=BGU=100 mg/dl, MBTS=0, PMA=false and the correction bolus stack is empty.

At step 112, the control circuit 14 executes the correction bolus stack processing routine of FIG. 5. Since the correction bolus stack is empty, execution of the routine is returned to step 112 of the algorithm 100. Thereafter at step 114, the control circuit 14 executes the meal bolus time processing routine of FIG. 6. Since the meal bolus time stamp, MBTS, is zero (i.e., not "set"), step 170 of the meal bolus time processing routine advances directly to step 178 where execution of the routine is returned to step 114 of the algorithm 100.

At step 116, the control circuit 14 executes the meal compensation bolus processing routine of FIG. 7. Since the carbohydrate estimate, CE, entered by the user at step 106 is zero, step 180 of the meal compensation bolus processing routine advances to step 190 where the control circuit 14 sets the meal compensation insulin bolus quantity, MB, equal to zero. Thereafter at step 192, execution of the routine is returned to step 116 of the algorithm 100.

At step 118, the control circuit 14 executes the correction bolus processing routine of FIGS. 8A and 8B. Since the blood glucose measurement, BGM, is 160 mg/dl, and the bolus trigger, BT, is 100 mg/dl, the control circuit 14 proceeds to execute step 234, and computes $\Delta$BG=160 mg/dl−100 mg/dl=60 mg/dl, CB=(60 mg/dl)/(40 mg/dl/I.U.)=1.5 I.U. and BGU=100 mg/dl+60 mg/dl=160 mg/dl. Also at step 234, the control circuit 14 enters the correction bolus time stamp, CBTS=T0, and the corresponding $\Delta$BG=60 mg/dl into the correction bolus stack to indicate that a first correction insulin bolus lock-out time period, LOT1, is now in effect with a corresponding $\Delta$BG=60 mg/dl as shown by the shaded region 300. Since the previous meal active flag, PMA, is "false" and the carbohydrate estimate, CE, is not greater than TCI, execution of the correction bolus processing routine advances to step 226 where the control circuit 14 is operable to set BT=160 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, the control circuit 14 is operable to set TB=1.5 I.U. Thereafter at step 256, execution of the routine is returned to step 120 of the algorithm 100.

Since no warnings are set, the algorithm 100 advances to step 134 where the display 88 (see, for example, FIG. 4E) displays a total insulin bolus quantity of 1.5 I.U. With no adjustment levels defined, the user accepts the initial results and the algorithm 100 advances to step 140 to display the final results, e.g., via the display 90 of FIG. 4F. The user accepts the total recommended insulin bolus quantity of 1.5 I.U., and execution of the algorithm 100 is terminated after storing current values of the parameter set. The recommended insulin bolus quantity of 1.5 I.U. is then administered to the user.

At time T1, the user again executes the algorithm 100 and enters at step 106 BGM=BGM$_1$=160 mg/dl and CE=0. Thereafter at step 112, the correction bolus stack processing routine is called. Since T0+120 minutes is not older than T1, the correction bolus stack entry is not processed for removal and execution of the routine returns to step 112 of the algorithm 100. Steps 114 and 116 provide no new information, and execution of the correction bolus processing routine at step 118 leads to step 236 where, since BGM=BT, the control circuit 14 is operable to set CB=0, and then to step 226 where the control circuit 14 is again operable to set BT=160 mg/dl. Since MB=CB=0, execution of the total insulin bolus processing routine at step 120 yields a total recommended insulin bolus quantity of zero.

At time T2, the user again executes the algorithm 100 and enters at step 106 BGM=BGM$_2$=190 mg/dl and CE=0. Thereafter at step 112, the correction bolus stack processing routine is called. Since T0+120 minutes is not older than T2, the correction bolus stack entry is not processed for removal and execution of the routine returns to step 112 of the algorithm 100. Steps 114 and 116 provide no new information, and execution of the correction bolus processing routine at step 118 leads to step 234 where the control circuit 14 is operable to compute ΔBG=190 mg/dl−160 mg/dl=30 mg/dl, CB=(30 mg/dl)/(40 mg/dl/I.U.)=0.75 I.U. and BGU=160 mg/dl+30 mg/dl=190 mg/dl. Also at step 234, the control circuit 14 enters the correction bolus time stamp, CBTS=T2, and the corresponding ΔBG=30 mg/dl into the correction bolus stack to indicate that a second correction insulin bolus lock-out time period, LOT2, is now in effect with a corresponding ΔBG=30 mg/dl as shown by the shaded regions 302A and 302B. Execution of the correction bolus processing routine then advances to step 226 where the control circuit 14 is operable to set BT=190 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, the control circuit 14 is operable to set TB=0.75 I.U. Thereafter at step 256, execution of the routine is returned to step 120 of the algorithm 100.

Since no warnings are set, the algorithm 100 advances to step 134 where the display 88 (see, for example, FIG. 4E) displays a total insulin bolus quantity of 0.75 I.U. With no adjustment levels defined, the user accepts the initial results and the algorithm 100 advances to step 140 to display the final results, e.g., via the display 90 of FIG. 4F. The user accepts the total recommended insulin bolus quantity of 0.75 I.U., and execution of the algorithm 100 is terminated after storing current values of the parameter set. The recommended insulin bolus quantity of 0.75 I.U. is then administered to the user. It will be appreciated that the control circuit 14 may be configured to round the total recommended insulin bolus quantity to a nearest specified incremental value. For example, the control computer 14 may be configured to compute the total insulin bolus quantity, as well as any correction insulin bolus quantity, CB, and/or meal compensation bolus quantity, MB, to the nearest one-tenth I.U. In this example, the display 90 would thus be configured to display as the total insulin bolus quantity 0.8 I.U. or 0.7 I.U., depending upon whether the control circuit 14 is configured to round up or round down. As another example, administering of the total insulin bolus may be carried out via an insulin pump or other automatic dosing unit, and in this example the dosing quantities may be available only in predetermine increments, e.g., 0.2 I.U. increments. In this example, such an automatic dosing unit may then dose 0.8 I.U. or 0.6 I.U. depending upon whether the control circuit 14 is configured to round up or round down. In any case, the control circuit 14 may be configured to require the user to manually accept or change the total recommended insulin bolus quantity before it is administered.

At a time between T3 and T4, the user again executes the algorithm 100 and enters at step 106 BGM=BGM$_3$=160 mg/dl and CE=0. Thereafter at step 112, the correction bolus stack processing routine is called. Since T0+120 minutes is not older than the current time (now between T3 and T4), the first correction bolus stack entry is not processed for removal, and since T2+120 minutes is not older than the current time, the second correction bolus stack entry is also not processed for removal. Execution of the routine then returns to step 112 of the algorithm 100. Steps 114 and 116 again provide no new information, and execution of the correction bolus processing routine at step 118 leads to step 236 where, since BGM<BT, the control circuit 14 is operable to set CB=0, and then to step 226 where the control circuit 14 is again operable to set BT=190 mg/dl. Since MB=CB=0, execution of the total insulin bolus processing routine at step 120 yields a total recommended insulin bolus quantity of zero.

At time T5, the user again executes the algorithm 100 and enters at step 106 BGM=BGM$_4$=160 mg/dl and CE=0. Thereafter at step 112, the correction bolus stack processing routine of FIG. 5 is called. Since T0+120 minutes is older than T5, the correction bolus stack entry having CBTS=T0, corresponding to the correction insulin bolus lock-out time period, LOT1, is processed via steps 154 and 156 by subtracting the corresponding ΔBG value associated with CBTS=T0 (60 mg/dl) from the current upper blood glucose target, BGU (currently 190 mg/dl), to yield BGU=130 mg/dl, and also subtracting this ΔBG value from the current bolus trigger, BT, (currently 190 mg/dl), to yield BT=130 mg/dl, and to then mark the correction bolus stack entry having CBTS=T0 for deletion from the correction bolus stack. Since T2+120 minutes is not older than T5, the second correction bolus stack entry is not processed for removal. Thereafter at step 160, the first correction bolus stack entry, i.e., that having CBTS=T0, is deleted from the correction bolus stack so that only one correction bolus stack entry now remains, i.e., that having CBTS=T2 and ΔBG=30 mg/dl. Thereafter at step 162, execution of the routine is returned to step 112 of the algorithm 100. Steps 114 and 116 again provide no new information, and execution of the correction bolus processing routine at step 118 leads to step 234 where the control circuit 14 is operable to compute ΔBG=160 mg/dl-130 mg/dl=30 mg/dl, CB=(30 mg/dl)/(40 mg/dl/I.U.)=0.75 I.U. and BGU=130 mg/dl+30 mg/dl=160 mg/dl. Also at step 234, the control circuit 14 enters the correction bolus time stamp, CBTS=T5, and the corresponding ΔBG=30 mg/dl into the correction bolus stack to indicate that a third correction insulin bolus lock-out time period, LOT3, is now in effect with a corresponding ΔBG=60 mg/dl as shown by the shaded blocks 304A and 304B. Execution of the correction bolus processing routine then advances to step 226 where the control circuit 14 is operable to set BT=160 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, the control circuit 14 is operable to set TB=0.75 I.U. Thereafter at step 256, execution of the routine is returned to step 120 of the algorithm 100.

Since no warnings are set, the algorithm 100 advances to step 134 where the display 88 (see, for example, FIG. 4E) displays a total insulin bolus quantity of 0.75 I.U. With no adjustment levels defined, the user accepts the initial results and the algorithm 100 advances to step 140 to display the final results, e.g., via the display 90 of FIG. 4F. The user accepts the total recommended insulin bolus quantity of 0.75 I.U., and execution of the algorithm 100 is terminated after storing current values of the parameter set. The recommended insulin bolus quantity of 0.75 I.U. is then administered to the user near time T5.

At time T7, the user again executes the algorithm 100 and enters at step 106 BGM=$BGM_5$=125 mg/dl and CE=0. Thereafter at step 112, the correction bolus stack processing routine is called. Since T2+120 minutes is older than T7, the correction bolus stack entry having CBTS=T2 is processed via steps 154 and 156 by subtracting the corresponding ΔBG value associated with CBTS=T2 (30 mg/dl) from the current upper blood glucose target, BGU (currently 160 mg/dl), to yield BGU=130 mg/dl, and also subtracts this ΔBG value from the bolus trigger (currently 160 mg/dl), to yield BT=130 mg/dl, and to then mark the correction bolus stack entry having CBTS=T2 for deletion from the correction bolus stack. Since T5+120 minutes is not older than T7, the remaining correction bolus stack entry is not processed for removal. Thereafter at step 160, the correction bolus stack entry having CBTS=T2, is deleted from the correction bolus stack so that only one correction bolus stack entry now remains, i.e., that having CBTS=T5 and ΔBG=30 mg/dl. Thereafter at step 162, execution of the routine is returned to step 112 of the algorithm 100. Execution of the routine then returns to step 112 of the algorithm 100. Steps 114 and 116 again provide no new information, and execution of the correction bolus processing routine at step 118 leads to step 236 where, since BGM<BT, the control circuit 14 is operable to set CB=0, and then to step 226 where the control circuit 14 is again operable to set BT=130 mg/dl. Since MB=CB=0, execution of the total insulin bolus processing routine at step 120 yields a total recommended insulin bolus quantity of zero.

EXAMPLE 2

Figure 11:
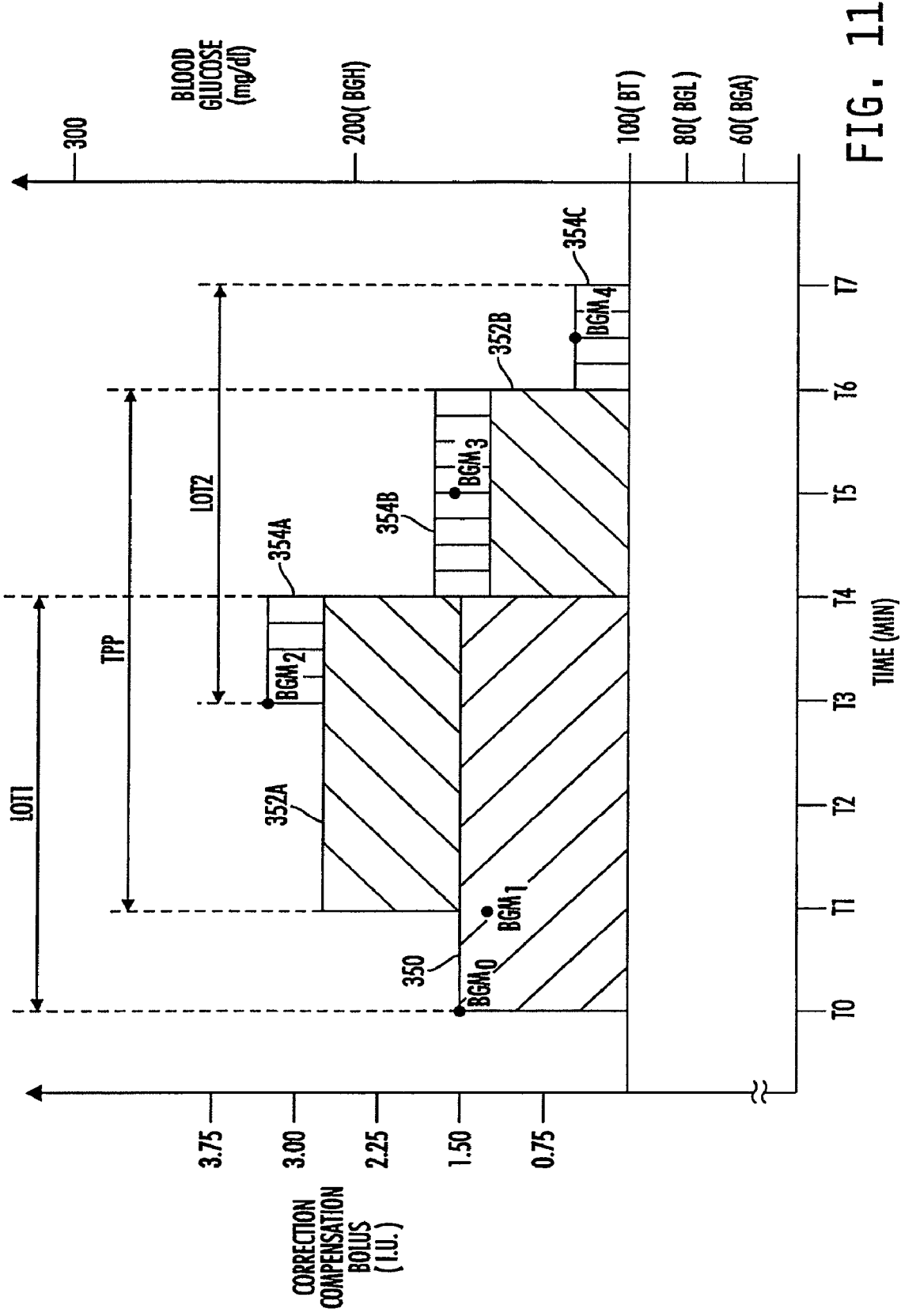
FIG. 11 is a plot of blood glucose and correction/compensation bolus vs. time illustrating another example of the operation of the insulin bolus recommendation algorithm of FIG. 3.

With the aid of FIG. 11, another example of the operation of the algorithm 100 will now be provided. In this example, a meal or snack will be ingested at or around time T1, and this example accordingly includes a calculation and recommendation of a meal compensation insulin bolus quantity. This example again presumes that the initialization or set up process illustrated in FIGS. 2A-2N and 2P-2Q has previously been executed, resulting in the example calculation factors, general parameters and optional parameters applicable during the illustrated time frame and shown in the following Table 2:

TABLE 2

| FACTOR OR PARAMETER | VALUE |
| --- | --- |
| BGU | 100 mg/dl |
| BGA | 60 mg/dl |
| BGL | 80 mg/dl |
| BGH | 200 mg/dl |
| MF | 1.0 I.U./10 gr. carbohydrates |
| IS | 40 mg/dl/I.U. |
| ΔPP | 50 mg/dl |
| TCI | 10 gr |
| TPP | 150 min |
| LOT | 120 min |
| Adjustment Level 1/3 | 0% |
| Adjustment Level 2/3 | 0% |
| Adjustment Level 3/3 | 0% |

Referring now to FIG. 11, a plot of blood glucose and correction-compensation bolus vs. time illustrating this example is shown. With the set up complete, the algorithm 100 prompts the user at step 106 to input a current blood glucose measurement, BGM, and a carbohydrate estimate, CE. At time T0, the user obtains a blood glucose measurement, $BGM_0$, and accordingly enters in the display 80 a BGM of 160 mg/dl. Since no meals or snacks will be ingested at or near T0, the user also enters in the display 80 a CE of 0 gr. Thereafter at step 108, the control circuit 14 retrieves the parameter set, corresponding to the information in Table 2, from the database stored in the memory unit 20. At step 110, the control circuit 14 also retrieves current values of the bolus trigger, BT, the upper blood glucose target, BGU, the meal bolus time stamp, MBTS, and the previous meal active flag, PMA, as well as the correction bolus stack. For the first execution of the algorithm 100, BT=BGU=100 mg/dl, MBTS=0, PMA=false and the correction bolus stack is empty.

At step 112, the control circuit 14 executes the correction bolus stack processing routine of FIG. 5. Since the correction bolus stack is empty, execution of the routine is returned to step 112 of the algorithm 100. Thereafter at step 114, the control circuit 14 executes the meal bolus time processing routine of FIG. 6. Since the meal bolus time stamp, MBTS, is zero (i.e., not "set"), step 170 of the meal bolus time processing routine advances directly to step 178 where execution of the routine is returned to step 114 of the algorithm 100.

At step 116, the control circuit 14 executes the meal compensation bolus processing routine of FIG. 7. Since the carbohydrate estimate, CE, entered by the user at step 106 is zero, step 180 of the meal compensation bolus processing routine advances to step 190 where the control circuit 14 sets the meal compensation insulin bolus quantity, MB, equal to zero. Thereafter at step 192, execution of the routine is returned to step 116 of the algorithm 100.

At step 118, the control circuit 14 executes the correction bolus processing routine of FIGS. 8A and 8B. Since the blood glucose measurement, BGM, is 160 mg/dl, and the bolus trigger, BT, is 100 mg/dl, the control circuit 14 proceeds to execute step 234, and computes ΔBG=160 mg/dl−100 mg/dl=60 mg/dl, CB=(60 mg/dl)/(40 mg/dl/I.U.)=1.5 I.U. and BGU=100 mg/dl+60 mg/dl=160 mg/dl. Also at step 234, the control circuit 14 enters the correction bolus time stamp, CBTS=T0, and the corresponding ΔBG=60 mg/dl into the correction bolus stack to indicate that a first correction insulin bolus lock-out time period, LOT1, is now in effect with a corresponding ΔBG=60 mg/dl as shown by the shaded region 350. Since the previous meal active flag, PMA, is "false" and the carbohydrate estimate, CE, is not greater than TCI, execution of the correction bolus processing routine advances to step 226 where the control circuit 14 is operable to set BT=160 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, the control circuit 14 is operable to set TB=1.5 I.U. Thereafter at step 256, execution of the routine is returned to step 120 of the algorithm 100.

Since no warnings are set, the algorithm 100 advances to step 134 where the display 88 (see, for example, FIG. 4E) displays a total insulin bolus quantity of 1.5 I.U. With no adjustment levels defined, the user accepts the initial results and the algorithm 100 advances to step 140 to display the final results, e.g., via the display 90 of FIG. 4F. The user accepts the total recommended insulin bolus quantity of 1.5 I.U., and execution of the algorithm 100 is terminated after storing current values of the parameter set. The recommended insulin bolus quantity of 1.5 I.U. is then administered to the user.

At time T1, the user again executes the algorithm 100 and enters at step 106 BGM=BGM$_1$=150 mg/dl. The user plans to shortly ingest a meal or snack having approximately 12 grams of carbohydrates, and the user therefore also enters at step 160 CE=12. Thereafter at step 112, the correction bolus stack processing routine is called. Since T0+120 minutes is not older than T1, the correction bolus stack entry is not processed for removal and execution of the routine returns to step 112 of the algorithm 100. Thereafter at step 114, the control circuit 14 executes the meal bolus time processing routine of FIG. 6. Since the meal bolus time stamp, MBTS, is zero (i.e., not "set"), step 170 of the meal bolus time processing routine advances directly to step 178 where execution of the routine is returned to step 114 of the algorithm 100.

At step 116, the control circuit 14 executes the meal compensation bolus processing routine of FIG. 7. Since the carbohydrate estimate, CE, entered by the user at step 106 is greater than zero, step 180 of the meal compensation bolus processing routine advances to step 182 where the control circuit 14 is operable to compute a meal compensation insulin bolus quantity, MB=(12 gr.)*(1.0 I.U./10 gr. carbohydrates) =1.2 I.U. Thereafter, since CE>TCI, the control circuit 14 is operable at step 186 to set the post-prandial blood glucose increase value $\Delta$BGPP=50 mg/dl, and thereafter at step 188 to set the meal bolus time stamp MBTS=T1 to indicate that a post-prandial lock-out time period, TPP, is now in effect with a corresponding $\Delta$BGPP=50 mg/dl as shown by the shaded region 352A and 352B. Thereafter at step 192, execution of the routine is returned to step 116 of the algorithm 100.

At step 118, the control circuit 14 executes the correction bolus processing routine of FIGS. 8A and 8B. Since the blood glucose measurement, BGM, is 150 mg/dl and BT=160 mg/dl, the control circuit 14 proceeds to execute step 236 and sets the correction insulin bolus quantity CB=0. Thereafter at step 238, since the previous meal active flag, PMA, is "false", execution of the correction insulin bolus processing routine advances to step 220. Since CE>TCI, the control circuit 14 is operable at step 222 to set the previous meal active flag, PMA, to "true", and thereafter at step 224 to compute the bolus trigger, BT=MAX(160 mg/dl, 150 mg/dl+50 mg/dl)=200 mg/dl. Thereafter at step 242, execution of the routine is returned to step 118 of the algorithm 100.

At step 120, the control circuit 14 executes the total insulin bolus processing routine of FIG. 9. Since the correction insulin bolus quantity, CB, is zero, the control circuit 14 is operable to set TB=MB=1.2 I.U. Thereafter at step 256, execution of the routine is returned to step 120 of the algorithm 100.

Since no warnings are set, the algorithm 100 advances to step 134 where the display 88 (see, for example, FIG. 4E) displays a total insulin bolus quantity of 1.2 I.U. With no adjustment levels defined, the user accepts the initial results and the algorithm 100 advances to step 140 to display the final results, e.g., via the display 90 of FIG. 4F. The user accepts the total recommended insulin bolus quantity of 1.2 I.U., and execution of the algorithm 100 is terminated after storing current values of the parameter set. The recommended insulin bolus quantity of 1.2 I.U. is then administered to the user.

At time T3, the user again executes the algorithm 100 and enters at step 106 BGM=BGM$_2$=220 mg/dl and CE=0. Thereafter at step 112, the correction bolus stack processing routine is called. Since T0+120 minutes is not older than T2, the correction bolus stack entry is not processed for removal and execution of the routine returns to step 112 of the algorithm 100. At step 114, the control circuit executes the meal bolus time processing routine of FIG. 6. Since T1+150 minutes (TPP) is not older than T2, execution of the routine returns to step 114 of the algorithm 100. At step 116 of the algorithm 100, the control circuit 14 executes the meal compensation bolus processing algorithm of FIG. 7. Since CE is now not greater than zero, the control circuit 14 is operable to set the meal compensation insulin bolus quantity, MB, equal to zero. Thereafter at step 192, execution of the routine is returned to step 116 of the algorithm 100. At step 118 of the algorithm 100, the control circuit 14 is operable to execute the correction bolus processing routine of FIGS. 8A and 8B. Since BGM=BGM$_2$>BGH, the control circuit 14 sets the warning to the high blood glucose warning text. Thereafter at step 232, since BGM$_2$=220 mg/dl is greater than BT=200 mg/dl, execution of the routine advances to step 234 where the control circuit 14 is operable to compute $\Delta$BG=220 mg/dl−200 mg/dl=20 mg/dl, CB=(20 mg/dl)/(40 mg/dl/I.U.) =0.5 I.U. and BGU=160 mg/dl+20 mg/dl=180 mg/dl. Also at step 234, the control circuit 14 enters the correction bolus time stamp, CBTS=T3, and the corresponding $\Delta$BG=20 mg/dl into the correction bolus stack to indicate that a second correction insulin bolus lock-out time period, LOT2, is now in effect with a corresponding $\Delta$BG=20 mg/dl as shown by the shaded regions 354A, 354B and 354C. Since the previous meal active flag, PMA, is now "true", execution of the correction bolus processing routine then advances to step 240 where the control circuit 14 is operable to set BT=180 mg/dl+ 50 mg/dl=230 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, the control circuit 14 is operable to set TB=CB=0.5 I.U. Thereafter at step 256, execution of the routine is returned to step 120 of the algorithm 100.

Since the high blood glucose warning is set, the algorithm 100 advances to step 124 where the display 86 (see, for example, FIG. 4D) displays a high blood glucose warning. At step 126, the user acknowledges the warning, and a time stamp of this acknowledgement is saved in the memory unit 20 at step 128. Since the warning does not correspond to a hypoglycemia alert, the algorithm 100 advances to step 134 where the display 88 (see, for example, FIG. 4E) displays a total insulin bolus value of 0.5 I.U. With no adjustment levels defined, the user accepts the initial results and the algorithm 100 advances to step 140 to display the final results, e.g., via the display 90 of FIG. 4F. The user accepts the total recommended insulin bolus quantity of 0.5 I.U., and execution of the algorithm 100 is terminated after storing current values of the parameter set. The recommended insulin bolus quantity of 0.5 I.U. is then administered to the user.

At time T5, the user again executes the algorithm 100 and enters at step 106 BGM=BGM$_3$=160 mg/dl and CE=0. Thereafter at step 112, the correction bolus stack processing routine of FIG. 5 is called. Since T0+120 minutes is older than T5, the correction bolus stack entry having CBTS=T0, corresponding to the correction insulin bolus lock-out time period, LOT1, is processed via steps 154 and 156 by subtracting the corresponding $\Delta$BG value associated with CBTS=T0 (60 mg/dl) from the current upper blood glucose target, BGU (currently 180 mg/dl), to yield BGU=120 mg/dl, and also subtracting this $\Delta$BG value from the bolus trigger (currently 220 mg/dl), to yield BT=160 mg/dl, and to then mark the correction bolus stack entry having CBTS=T0 for deletion from the correction bolus stack. Since T3+120 minutes is not older than T5, the second correction bolus stack entry is not processed for removal. Thereafter at step 160, the first correction bolus stack entry, i.e., that having CBTS=T0, is deleted from the correction bolus stack so that only one correction bolus stack entry now remains, i.e., that having CBTS=T2 and ΔBG=20 mg/dl. Thereafter at step 162, execution of the routine is returned to step 112 of the algorithm 100.

At step 114, the control circuit 14 executes the meal bolus time processing routine of FIG. 6. Since T1+150 minutes (TPP) is not older than T5, execution of the routine returns to step 114 of the algorithm 100. At step 116 of the algorithm 100, the control circuit 14 executes the meal compensation bolus processing algorithm of FIG. 7. Since CE is not greater than zero, the control circuit 14 is operable to set the meal compensation insulin bolus quantity, MB, equal to zero. Thereafter at step 192, execution of the routine is returned to step 116 of the algorithm 100. At step 118 of the algorithm 100, the control circuit 14 is operable to execute the correction bolus processing routine of FIGS. 8A and 8B. At step 232, since $BGM_3=160$ mg/dl is not greater than BT=160 mg/dl, execution of the routine advances to step 236 where the control circuit 14 is operable to set the correction insulin bolus quantity, CB, equal to zero. Since the previous meal active flag, PMA, is still "true", execution of the correction bolus processing routine then advances to step 240 where the control circuit 14 is operable to set BT=120 mg/dl+50 mg/dl=170 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, and the correction insulin bolus quantity, CB, is zero the control circuit 14 is operable to set TB=0. Since MB=CB=0, execution of the total insulin bolus processing routine at step 120 yields a total recommended insulin bolus quantity of zero.

At a time between T6 and T7, the user again executes the algorithm 100 and enters at step 106 $BGM=BGM_4=120$ mg/dl and CE=0. Thereafter at step 112, the correction bolus stack processing routine of FIG. 5 is called. Since T3+120 minutes is not older than the current time, the correction bolus stack entry corresponding to CBTS=T3 is not processed for removal. Thereafter at step 162, execution of the routine is returned to step 112 of the algorithm 100.

At step 114, the control circuit 14 executes the meal bolus time processing routine of FIG. 6. Since T1+150 minutes (TPP) is older than the current time, the post-prandial lock-out time period, TPP, has expired and the control circuit 14 subtracts the post-prandial blood glucose increase value, ΔBGPP, from the current value of the bolus trigger, BT, (currently 170 mg/dl) at step 172 to yield BT=120 mg/dl, and thereafter at step 174 sets the post-prandial blood glucose increase value, ΔBGPP, equal to zero. At step 176 the control circuit 14 sets the previous meal active flag, PMA, to "false" and clears the meal bolus time stamp, MBTS. Thereafter at step 178, execution of the routine returns to step 114 of the algorithm 100. At step 116 of the algorithm 100, the control circuit 14 executes the meal compensation bolus processing algorithm of FIG. 7. Since CE is not greater than zero, the control circuit 14 is operable to set the meal compensation insulin bolus quantity, MB, equal to zero. Thereafter at step 192, execution of the routine is returned to step 116 of the algorithm 100. At step 118 of the algorithm 100, the control circuit 14 is operable to execute the correction bolus processing routine of FIGS. 8A and 8B. At step 232, since $BGM_4=120$ mg/dl is not greater than BT=170 mg/dl, execution of the routine advances to step 236 where the control circuit 14 is operable to set the correction insulin bolus quantity, CB, equal to zero. Since the previous meal active flag, PMA, is now "false", execution of the correction bolus processing routine then advances to step 226 where the control circuit 14 is operable to set BT=BGU=120 mg/dl. Thereafter at step 242, execution of the routine is returned to step 118 of the algorithm 100.

At step 120, the control circuit 14 executes the total insulin bolus processing routine of FIG. 9. Since the meal compensation insulin bolus quantity, MB, is zero, and the correction insulin bolus quantity, CB, is zero the control circuit 14 is operable to set TB=0. Since MB=CB=0, execution of the total insulin bolus processing routine at step 120 yields a total recommended insulin bolus quantity of zero.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A system for recommending insulin bolus quantities to an insulin user, the system comprising:
   a data input device for providing information from the user,
   a display for displaying information to the user, and
   a control circuit including a memory having a blood glucose target for the user stored therein, the control circuit receiving a current blood glucose value of the user from information provided by the user via the data input device, the control circuit determining a recommended insulin bolus quantity if the current blood glucose value exceeds the blood glucose target, computing a difference value as the current blood glucose value less the blood glucose target, and increasing the blood glucose target by the difference value for a lock-out time period if the difference value is positive, the control circuit controlling the display to display the recommended insulin bolus quantity to the user.

2. The system of claim 1 wherein the control circuit is configured to repeatedly receive a current blood glucose value of the user from information provided by the user via the data input device, determine a recommended insulin bolus quantity if the current blood glucose value exceeds the blood glucose target, compute a difference value as the current blood glucose value less the blood glucose target, increase the blood glucose target by the difference value for a lock-out time period if the difference value is positive, and control the display to display the recommended insulin bolus quantity to the user.

3. The system of claim 1 wherein the control circuit is configured to control the display to display a high blood glucose warning if the current blood glucose value is greater than a high blood glucose warning value.

4. The system of claim 1 wherein the control circuit is configured to control the display to display a low blood glucose warning if the current blood glucose value is less than a low blood glucose warning value.

5. The system of claim 1 wherein the control circuit is configured to control the display to display a low blood glucose alert if the current blood glucose value is less than a low blood glucose alert value.

6. A system for recommending insulin bolus quantities to an insulin user, the system comprising:
   a data input device for providing information from the user,
   a display for displaying information to the user, and
   a control circuit including a memory having a blood glucose target for the user stored therein, the control circuit receiving a carbohydrate value from information provided by the user via the data input device, the carbohydrate value indicative of a quantity of carbohydrates that will be subsequently ingested by the user, the control circuit determining a recommended compensation insulin bolus quantity as a function of the carbohydrate value and increasing the blood glucose target by a post-prandial increase value to produce a first modified blood glucose target for a post-prandial lock-out time period if the carbohydrate value exceeds a threshold value, the control circuit controlling the display to display the recommended compensation insulin bolus quantity to the user.

7. The system of claim 6 wherein the control circuit receives a current blood glucose value of the user from information provided by the user via the data input device after the recommended compensation insulin bolus quantity is administered to the user, the control circuit determining a recommended correction insulin bolus quantity if the current blood glucose value exceeds the first modified blood glucose target, computing a difference value as the current blood glucose value less the first modified blood glucose target, and increasing the first modified blood glucose target by the difference value to produce a second modified blood glucose target for a correction lock-out time period if the difference value is positive, the control circuit controlling the display to display the recommended correction insulin bolus quantity to the user.

8. The system of claim 7 wherein the control circuit is configured to control the display to display a high blood glucose warning if the current blood glucose value is greater than a high blood glucose warning value.

9. The system of claim 7 wherein the control circuit is configured to control the display to display a low blood glucose warning if the current blood glucose value is less than a low blood glucose warning value.

10. The system of claim 7 wherein the control circuit is configured to control the display to display a low blood glucose alert if the current blood glucose value is less than a low blood glucose alert value.

11. A system for recommending insulin bolus quantities to an insulin user, the system comprising:

a data input device for providing information from the user, a display for displaying information to the user, and a control circuit including a memory having a blood glucose target for the user stored therein, the control circuit receiving a current user blood glucose value and a carbohydrate value from information provided by the user via the data input device, the carbohydrate value indicative of a quantity of carbohydrates that will be subsequently ingested by establishing a blood glucose target for the user, the control circuit determining a recommended compensation insulin bolus quantity as a function of the carbohydrate value, and determining a recommended correction insulin bolus quantity if the current blood glucose value exceeds the blood glucose target, the control circuit increasing the blood glucose target by a post-prandial increase value for a post-prandial lock-out time period if the carbohydrate value exceeds a threshold value and increasing the blood glucose target by a difference value, corresponding to the current blood glucose value less the blood glucose target, for a correction lock-out time period if the difference value is positive, the control circuit controlling the display to display the recommended compensation and correction insulin bolus quantities to the user.

12. The system of claim 11 wherein the control circuit is configured to control the display to display a high blood glucose warning if the current blood glucose value is greater than a high blood glucose warning value.

13. The system of claim 11 wherein the control circuit is configured to control the display to display a low blood glucose warning if the current blood glucose value is less than a low blood glucose warning value.

14. The system of claim 11 wherein the control circuit is configured to control the display to display a low blood glucose alert if the current blood glucose value is less than a low blood glucose alert value.

* * * * *